(12) United States Patent
Muggleton et al.

(10) Patent No.: US 11,670,275 B2
(45) Date of Patent: *Jun. 6, 2023

(54) DISTRIBUTED NETWORK OF COMMUNICATIVELY COUPLED NOISE MONITORING AND MAPPING DEVICES

(71) Applicant: Honeywell International Inc., Charlotte, NC (US)

(72) Inventors: Neal Muggleton, Morris Plains, NJ (US); Trym Holter, Morris Plains, NJ (US); Viggo Henriksen, Morris Plains, NJ (US); Claes Haglund, Morris Plains, NJ (US); May Wilson, Morris Plains, NJ (US); John Jenkins, Morris Plains, NJ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 25 days.

This patent is subject to a terminal disclaimer.

(21) Appl. No.: 17/120,877

(22) Filed: Dec. 14, 2020

(65) Prior Publication Data

US 2021/0097969 A1    Apr. 1, 2021

Related U.S. Application Data

(63) Continuation of application No. 16/479,272, filed as application No. PCT/US2018/017335 on Feb. 8, 2018, now Pat. No. 10,896,667.

(Continued)

(51) Int. Cl.
*G10K 11/178* (2006.01)
*G06F 16/29* (2019.01)
(Continued)

(52) U.S. Cl.
CPC ........ *G10K 11/17813* (2018.01); *G06F 16/29* (2019.01); *G10K 11/17881* (2018.01);
(Continued)

(58) Field of Classification Search
CPC .. A61F 2/06; A61F 11/06; A61F 11/08; A61F 2011/145; G01H 3/125;
(Continued)

(56) References Cited

U.S. PATENT DOCUMENTS 10,440,463 B2    10/2019 Jenkins et al.
10,896,667 B2 *  1/2021 Muggleton ............. G06F 16/29
(Continued)

FOREIGN PATENT DOCUMENTS

WO    2010/030889 A1    3/2010
WO    2018/148356 A1    8/2018

OTHER PUBLICATIONS

Communication Pursuant to Article 94(3) issued in European Application No. 18706612.1dated Oct. 7, 2021, 5 pages.
(Continued)

*Primary Examiner* — Harry S Hong
(74) *Attorney, Agent, or Firm* — Alston & Bird LLP

(57) ABSTRACT

Disclosed embodiments may relate to systems and methods for monitoring and/or mapping noise data from a plurality of noise monitoring devices. In some embodiments, the plurality of noise monitoring devices may include hearing protection devices configured to detect noise, and typically may communicate such noise data (which may also include location) so that the noise data can be pooled. The pooled noise data from the plurality of noise monitoring devices may then be used to the benefit of one or more of such noise monitoring devices.

20 Claims, 5 Drawing Sheets

Related U.S. Application Data

(60) Provisional application No. 62/457,298, filed on Feb. 10, 2017.

(51) Int. Cl.
| | | |
|---|---|---|
| *H04R 1/10* | (2006.01) | |
| *H04R 29/00* | (2006.01) | |
| *G06F 17/18* | (2006.01) | |

(52) U.S. Cl.
CPC ......... *H04R 1/1083* (2013.01); *H04R 29/004* (2013.01); *G06F 17/18* (2013.01); *H04R 2460/07* (2013.01)

(58) Field of Classification Search
CPC ... G06F 16/29; G06F 17/18; G10K 11/17813; G10K 11/17881; H04R 1/1083; H04R 1/406; H04R 29/00; H04R 29/004; H04R 29/008; H04R 2460/07
USPC .......................................... 381/56, 71.6, 72
See application file for complete search history.

(56) References Cited

U.S. PATENT DOCUMENTS

| | | |
|---|---|---|
| 2006/0262938 A1 | 11/2006 | Gauger et al. |
| 2007/0129828 A1 | 6/2007 | Lee et al. |
| 2007/0186656 A1 | 8/2007 | Goldberg et al. |
| 2008/0137873 A1 | 6/2008 | Goldstein |
| 2008/0159547 A1 | 7/2008 | Schuler et al. |
| 2008/0205660 A1 | 8/2008 | Goldstein |
| 2008/0212787 A1 | 9/2008 | Goldstein et al. |
| 2010/0135502 A1 | 6/2010 | Keady et al. |
| 2012/0321094 A1 | 12/2012 | Schiller et al. |
| 2013/0094658 A1 | 4/2013 | Holter |
| 2013/0101126 A1 | 4/2013 | Van et al. |
| 2014/0192990 A1 | 7/2014 | Cheng |
| 2015/0110278 A1 | 4/2015 | Andersen |
| 2015/0223000 A1 | 8/2015 | Bran et al. |
| 2015/0287421 A1 | 10/2015 | Benway et al. |
| 2015/0379994 A1 | 12/2015 | Goldstein et al. |
| 2016/0165340 A1 | 6/2016 | Benattar |
| 2017/0188166 A1 | 6/2017 | Eberbach et al. |
| 2018/0041847 A1 | 2/2018 | Umicevic |

OTHER PUBLICATIONS

Notification of Grant of Patent Right issued in Chinese Application No. 201880010225.1 dated Jul. 20, 2021, 7 pages.

CN Search Report dated Aug. 10, 2020 for CN Application No. 201880010225.1.

Communication pursuant to Rules 161(1) and 162 dated Sep. 20, 2019, 3 pages.

English Translation of CN Office Action dated Aug. 21, 2020 for CN Application No. 201880010225.1.

International Search Report and Written Opinion for Application No. PCT/US2018/017335, dated May 9, 2018, 12 pages.

Non-Final Rejection dated Apr. 3, 2020 for U.S. Appl. No. 16/593,790.

Non-Final Rejection dated Jan. 11, 2019 for U.S. Appl. No. 16/003,297.

Non-Final Rejection dated Mar. 19, 2020 for U.S. Appl. No. 16/479,272.

Notice of Allowance and Fees Due (PTOL-85) dated Jul. 29, 2020 for U.S. Appl. No. 16/593,790.

Notice of Allowance and Fees Due (PTOL-85) dated May 29, 2019 for U.S. Appl. No. 16/003,297.

Notice of Allowance and Fees Due (PTOL-85) dated Oct. 15, 2020 for U.S. Appl. No. 16/479,272.

Notice of Allowance and Fees Due (PTOL-85) dated Oct. 19, 2020 for U.S. Appl. No. 16/593,790.

Notice of Allowance and Fees Due (PTOL-85) dated Oct. 30, 2020 for U.S. Appl. No. 16/593,790.

Notice of Allowance and Fees Due (PTOL-85) dated Sep. 16, 2020 for U.S. Appl. No. 16/479,272.

Office Action issued in Chinese Application No. 201880010225.1 dated Jan. 28, 2021, 3 pages.

U.S. Appl. No. 16/479,272, filed Jul. 19, 2019, U.S. Pat. No. 10,896,667, Patented.

* cited by examiner

DISTRIBUTED NETWORK OF COMMUNICATIVELY COUPLED NOISE MONITORING AND MAPPING DEVICES

CROSS-REFERENCE TO RELATED APPLICATIONS

The present application is a continuation of U.S. patent application Ser. No. 16/479,272, filed Jul. 19, 2019 and entitled "Distributed Network of Communicatively Coupled Noise Monitoring and Mapping Devices," which is a National Stage Entry of International Patent Application Serial No. PCT/US2018/017335, filed Feb. 8, 2018 and entitled "Distributed Network of Communicatively Coupled Noise Monitoring and Mapping Devices," which claims priority to, and the benefit of, U.S. Provisional Patent Application Ser. No. 62/457,298, filed Feb. 10, 2017 by Neal Muggleton, et al. and entitled "Distributed Network of Communicate Coupled Noise Monitoring and Mapping Devices," the entire disclosures of each of which are hereby incorporated herein by reference in their entireties for all purposes as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous industrial work environments, machinery and alarm speakers may periodically and/or continuously generate noise that can be harmful to worker's ears and potentially cause noise-induced hearing loss and/or hearing damage over short and/or prolonged exposure periods. The issue of potential hearing damage often arises in manufacturing and other industrial facilities, but may also arise in military settings, airport settings, and other work environments that involve potentially damaging noise exposure. The sounds generated by machines, speakers, or people may occur at different locations within a worksite and the level of noise may increase as the sound sources multiply and/or with the occurrence of an emergency event, such as an alarm tone having a higher frequency and level (e.g., decibel) in an emergency event compared to the sound frequency and level in typical, non-emergency industrial work environments. Thus, to safeguard the hearing of people (such as workers, employees, customers, etc.) against harmful and/or prolonged noise exposure, the use of hearing protection may be implemented. The level of hearing protection can be measured in terms of decibel levels of exposure (dB) (e.g., differences in level of exposure) and corresponding noise reduction capability referred to as noise reduction rating (NRR).

SUMMARY

Embodiments of the present disclosure relate to systems and methods to monitor and map noise data from a plurality of noise monitoring devices (NMD) (e.g., specifically configured noise dosimeters, sound level meters, hearing protection devices (hpd), non-attenuating headsets, attenuating headsets, other sensor equipment (e.g., gas detectors) with noise monitoring capabilities (e.g., microphones), Personal Protection Equipment (PPE) with noise monitoring capabilities (e.g., PPE having integrated wearable sensors), and/or in some embodiments fixed noise monitoring devices—in other words, the NMD may comprise mobile (e.g., configured to be attached to, carried by, and/or worn by individual users/workers (e.g., personalized)) and/or fixed devices), which typically may be specifically configured and operable to communicatively couple (e.g., wired and/or wirelessly) to a central computer system (which is configured to be a non-generic particular machine) via a network. In some embodiments, the computer system is configured to receive the noise data (which may include measured sound values, location information, identifiers, and other information received from noise monitoring devices (such as classification of sound or other sensor data, for example)) from the plurality of noise monitoring devices, pool the noise detection data (such as by concatenating identifiers of each noise monitoring device), and create a noise map that is operable for output to a display (e.g., a display of a user equipment located at a facility in which the noise monitoring devices are located, which could in come embodiments include display of output from the noise map/computer on NMD (e.g., hpd) or other devices within the facility—for example, passive display means such as lighting which may provide a direct method of communication to the workers in the immediate surroundings and others who may or may not be wearing NMD/hpd), in some instances including hpd which could include lights indicative of noise level and/or lit floor tiles representative of noise level). In some embodiments, the noise map may be instantaneous (e.g., reflecting one (single) moment in time, for example all information/data at a particular instance and/or related to a specific sampling instance/time), dynamic (e.g., changing periodically to reflect current information or updated accumulated information/data (e.g., reflecting an average noise level over a pre-set time period, for example an average per minute, per five minutes, per 10 minutes, per fifteen minutes, per hour, per shift, or per day), for example based on sampling frequency rate), and/or cumulative over some set period of time. Typically, each instantaneous noise map (e.g., noise data for a particular time and/or sampling instance/time) would be stored in memory for some time period (e.g., for at least the longest of any time period(s) which might be used for any cumulative noise map purposes), such that any and all such noise maps (e.g., noise data) might be available to the system (for example, depending on the specific type of data needed for a particular usage/analysis). Noise monitoring devices may also be referred to as noise mapping devices (NMD). For example, a computer system may create a noise map in which noises (e.g., sound levels) between known noise data points (received from the plurality of noise monitoring devices of the system) are interpolated and correlated with known location identifiers on a generated digital noise map (a data structure configured to correspond with a predefined layout of a physical location, such as but not limited to a factory layout, construction site, commercial building, etc.). Once created, the computer system may push, via a network, the noise map to displays that are accessible to a user associated with at least one of the plurality of noise monitoring devices (such as a user wearing a hearing protection device that reported noise detection data to the central computer system) and/or to a supervisor or monitor personnel (for example at a central or remote location) and/or to any other networked device (such as a smart phone or smart watch).

For example, embodiments of a system of the present disclosure could comprise: (1) a plurality of noise monitoring devices (such as a NMD that is specifically configured as a hearing protection device that optionally has a hearing protection element (e.g., earmuff, earplug, or other element for sealing the ear canal or otherwise protecting the user from external noise)), wherein at least one noise monitoring device may include: at least one microphone electrically coupled to a processor that is configured to receive incoming noise signals via at least one microphone and then transform the noise signals into noise data that is collected for noise monitoring, a locator device (such as a global positioning receiver module, one or more short-range and/or long-range transceivers (e.g., operable for wireless communication at distances between 1 mm-100 m, and 1 mm-100 km respectively) coupled to the processor to determine location via trilateration, radio frequency identification transceivers, wi-fi transceiver, etc.) operable/configured to determine the noise monitoring device's location (such as the location of the NMD within a facility), and a transceiver (e.g., a radio transceiver configured for wireless communication and/or a wired transceiver for communicating noise data). In some embodiments, the system may further comprise (2) a remotely located computer system that is communicatively coupled, via the network, to the plurality of noise monitoring devices, the computer system comprising a transceiver coupled to a processor and a non-transitory memory, the non-transitory memory comprising an application that, upon execution, configures the computer system to: communicate with the plurality of noise monitoring devices and/or receive noise data from at least the NMD that provides hearing protection; pool the noise data communicated from the NMD (that provides hearing protection) and the plurality of noise monitoring devices; and based on the pooled noise data, generate a noise map. To generate an effective noise map, the system may sample noise at a rate suitable for the specific end use to which the noise map pooled data may be put. So for example, in some embodiments the noise monitoring device might detect noise at a rate from one minute, to 15 minutes, to hourly, to daily, depending on the specific usage envisioned for the data. More frequent sampling (for example once per second or even more frequently) may yield a higher data resolution, which might be advantageous in some embodiments (for example in uses related to moving noise sources). A plurality of NMD's could be communicatively connected with the computer system, and the computer system would use the detected noise data from one or more NMD's to generate a noise map. The computer system may be remotely located relative the plurality of noise monitoring devices (such as one or more NMD's that provide hearing protection), and the computer system can be configured to interpolate for areas of the noise map between the actual measured noise monitoring data points received by the computer from the NMDs (wherein the interpolation may in some instances be based on a model of the site, such that sound propagation can be calculated/estimated). The remotely located computer system may be operable to provide a display (e.g., a monitor screen) that is configured to present the noise map in a visual format (e.g., typically heat maps, which might show a layout of a facility and indicating intensity levels of sound at certain locations in the facility based on varying colors and brightness levels, where for example the higher intensity of noise is represented by a more concentrated color and/or brightness on the map relative low intensity noise locations on the map with darker colors and/or lower brightness). In some instances, the computer system might transmit the generated noise map to a plurality of displays (e.g., separate and apart from the computer system) which are located a predefined distance from the plurality of noise monitoring devices.

Such a noise map might then be used by the computer system and/or noise monitoring devices in a variety of ways, for example with interaction with one or more of the noise monitoring devices and/or sources of the noise. For example, data from the noise map could be used by the computer system, noise monitoring devices, and/or sources producing the noise in one or more of the following ways: (a) determine from noise data and/or the noise map (from the communicatively connected noise monitoring devices) if there is a moving noise source that might pose a physical hazard to users with limited hearing (e.g., due to possible hearing damage and/or the use of hearing protection) and warn users of a potential collision hazard; (b) detect an alarm and transmit/share alarm information with other hpd in the zone of alarm and/or related zone(s) (e.g., in proximity or abutting the alarm zone); (c) correlate user location (e.g., location of the NMD) with noise level and compare to database (e.g., containing specific hearing information/threshold for each device) to determine if a warning should be sent to a specific NMD (for example, if the specific device corresponds with a user profile indicating a sensitivity to noise and that user should not be exposed to such loud noise); (d) detect if a hpd is (in an adjacent zone and) moving towards a zone having noise in excess of the user's threshold; (e) for a new worker coming in that is wearing an NMD, determine the zone (of the noise map/facility) that the user will be entering and suggest/recommend (e.g., via an audible warning transmitted to that user's NMD) or provide (e.g., automatically dispense hearing protection via a proximate hearing protection dispenser) appropriate hpd based on their location within the noise map; (f) compare information on the location and type of NMD to the noise map, determine if the hearing protection provided by the NMD is insufficient/inadequate (e.g., hearing protection element of the NMD does not have active noise cancellation and/or not a high enough NRR), and transmit a warning to the NMD if the hearing protection is found inadequate; (g) generate an estimate of time (left/remaining) to spend in the zone (based on location, type of NMD that provides hearing protection, noise map, individualized user hearing information/threshold, and/or previous exposure (history) to noise) and transmit to the NMD; (h) use noise data (e.g., from the noise map) regarding a moving noise source to alter the set-up/configuration of NMD along the trajectory of the moving noise source. In some embodiments, the noise map could be used in combination with a worker location tracking system, such that the person/worker not wearing any noise monitoring NMD/hpd could still have their noise exposure data determined and stored by the computer by combining the worker's location throughout the work day compared with the noise levels available through the mapped data (e.g., from the NMD) at the time that such person/worker is located in a given area (with known noise level due to the noise map) (e.g., correlating such a worker's location with the measured noise data from other NMD). Other uses for the noise map data (such as population wide analysis of areas/zones within a facility that may need to be engineered to reduce noise emissions or using noise detection information for fault detection, for example to detect part or equipment failure based on noise level outside the expectation (e.g., range) for a zone/area (for example based on pre-knowledge of what an area/zone should sound like and/or based on specific frequency detection indicative of such a failure) and/or help locate such failures by correlating data from several noise monitoring devices, which can then be used to notify maintenance and/or NMD reacting to the environment by adjusting hear through and/or noise cancelling function's within the HPD and/or environmental (external) noise mapping) may also be contemplated, and are within the scope of this disclosure. Further details about embodiments of the present disclosure for use of the noise map are set forth below.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The use of the term "comprising" and the term "including", (as well as other forms such as "comprises", "includes", and "included") is not to be interpreted as limiting;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

Use of the term "exemplary" or an "example" is understood to refer to a non-exclusive example, and the use of such term means "serving as an example, instance, or illustration," and should not necessarily be construed as preferred or advantageous over other embodiments;

The terms "about" or "approximately" or the like, when used with a number, is understood to mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

In the following description, reference is made to the accompanying drawings that form a part hereof, and in which is shown by way of illustration specific embodiments which may be practiced. These embodiments are described in sufficient detail to enable those skilled in the art to practice the present disclosure, and it is to be understood that other embodiments may be utilized and that structural, logical and electrical changes may be made without departing from the scope of the present disclosure. The following description of example embodiments is, therefore, not to be taken in a limited sense.

Figure 1:
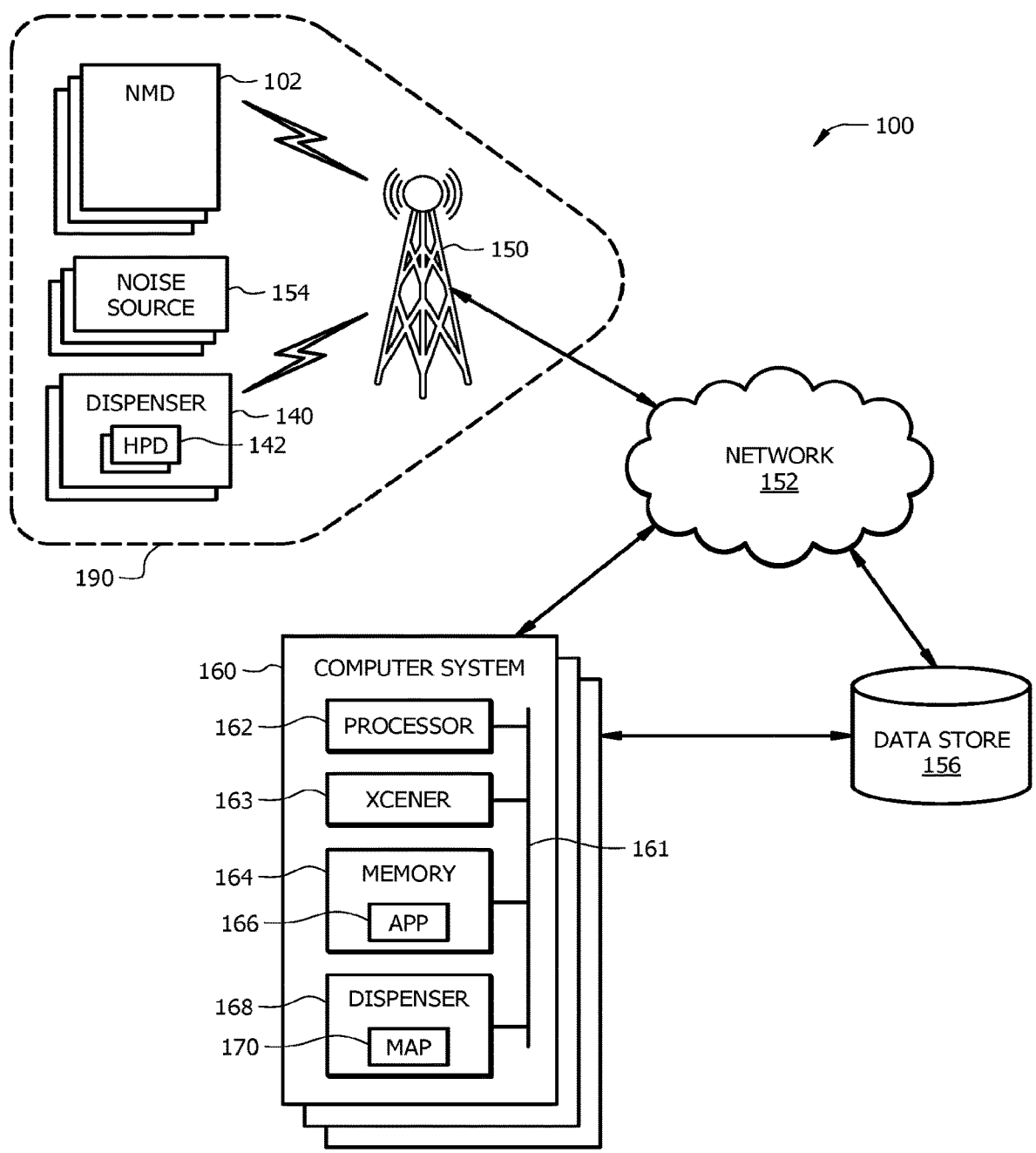
FIG. 1 is a diagram of a noise mapping and monitoring system according to an embodiment of the disclosure.

Turning now to FIG. 1, a noise monitoring and mapping system 100 is disclosed for implementation of embodiments of the present disclosure. System 100 comprises a plurality of noise monitoring devices (NMD) 102 (which may also be referred to as noise mapping devices NMD), at least one hearing protection dispenser 140 (hereinafter dispenser), and at least one noise source 154. The noise source 154 may be embodied by one or more sound/audio sources that produce sounds in work environments, such as machinery, vehicles, speakers, people, or equipment in manufacturing and industrial facilities, military settings, airport settings, and other work environments that involve potentially damaging noise exposure. A noise source, such as noise source 154, generates continuous and/or intermittent noise above a defined threshold for defined a time period (such as above 90 dB for at least 1 second). NMD's 102 and dispenser 140 are capable of wireless communication with each other and with one or more computer system(s) 160 via one or more network node(s) 150 (e.g., a wireless access point (WAP) and/or cell site). Each of the NMD's 102, dispenser 140, and network nodes 150 communicatively couple with the computer system 160 via a network 152. The computer system 160 may access datastore 156 via direct and/or indirect communicatively coupling, such at least some of the memory of datastore 156 being co-located with computer system 160 and/or being accessed via network 152. It is understood that, in some embodiments, the total number of NMD's 102, network nodes 150, dispensers 140, noise sources 154, computer systems 160, and datastores 156 may greater than the number of devices illustrated in FIG. 1 or at least some features discussed may be combined into fewer devices than illustrated in FIG. 1.

Embodiments of network 152 may comprise a public network, private network, wired network, wireless network, internet protocol network, core network, radio access network, or any combination thereof, and comply with standards of wireless communication protocol. Each network node 150 is configured to provide a wireless communication link(s) to and from at least the NMD's 102 and dispenser 140 according to at least one wireless communication standard, such as Long Term Evolution (LTE), Worldwide Interoperability for Microwave Access (WiMAX), High Speed. Packet Access (HSPA), Code Division Multiple Access (CDMA), Global System for Mobile Communication (GSM), Bluetooth, Wi-Fi (e.g., WAP using 802.11 standards), or any combination thereof. A network node 150 may, in some embodiments, be referred to according to the technology with which it supports, such as being referred to a wireless access point (WAP) for corresponding to an 802.11 wireless technology, an enhanced Node B (eNB) for corresponding to an LTE technology, a base transceiver station (BTS) for corresponding to a GSM technology, or another type of edge node used in wireless communications. In some embodiments, one or more network node 150 may comprise computer elements (e.g., processors, transceivers, antennas) that facilitate wireless communication and the elements may be distributed in a location and/or co-located in physical structures that are separate from other elements, but collectively comprise the network node 150 that is communicatively coupled (e.g., via wired and/or wireless communication paths) with the network 152.

Hearing protection dispenser 140 comprises a radio transceiver, processor, memory, and circuitry that dispenses hearing protection devices 142 in response to release messages sent by computer system 160. The dispenser 140 may be configured to provide hearing protection identifiers to computer system 160, where each hearing protection identifier is stored in memory and corresponds with one of the hearing protection devices 142 that is dispensed by a dispensing unit. For example, computer system 160 may communicate with dispenser 140 (via network node 150) to request how many hearing protection devices 142 are available for distribution. The dispenser 140 may transmit a list of hearing protection identifiers to application 166 in computer system 160. Computer system 160 may determine that one of the hearing protection devices 142 is suitable to mitigate hazardous noise within the predefined area 190, and thus send a release message to dispenser 140, with the release message comprising the identifier(s) of the hearing protection devices that should be released. For example, dispenser 140 may store a list of identifiers corresponding to twenty ear plugs that have an NRR rating of 32. Dispenser 140 may receive a release message, from computer system 160, comprising instructions to dispense three sets of earplugs (e.g., hearing protection devices 142). In some embodiments, the dispenser 140 may actuate a release mechanism that releases the hearing protection devices 142 (e.g., three sets of earplugs in this example) from a storage container. In some embodiments, dispenser 140 may dispense the hearing protection devices 142 in response to a user being within a defined proximity to the dispenser 140, such as by dispenser 140 communicating with an radio frequency identity (RFID) tag associated with the user and/or allowing a user to manually release the hearing protection device(s) 140 when the user's noise mapping device 102 is within five feet of the dispenser 140.

Computer system 160 may be occasionally referred to as a central server, and comprises a communication bus 161, processor 162, transceiver 163, memory 164 and display 168. Memory 164 stores mapping application 166 that configures processor 162 upon execution. It is understood that, in some embodiments, computer system 160 may comprise one or more servers and accesses noise data and records in datastore 156. Although display 168 is illustrated as being comprised within computer system 160, it is understood that display 168 may be a remote display that is remotely located from computer system 160, but remains operable to present a noise map 170 created by execution of application 166, as further discussed herein.

Continuing discussion of FIG. 1 with further reference to FIGS. 3A, 3B, 3C, and 3D, noise mapping devices 102 may be portable devices that are configured to sense environment sounds (e.g., environment noise), record the received sounds as a noise value corresponding to a level of noise (e.g., a value in units of dB), create a noise data record that comprises at least the noise value and a location marker at a time of the received sounds, determine a historical location marker based on a log stored in memory of the NMD 102, insert the historical location marker in the noise data record, and wirelessly transmit the noise data record to computer system 160 via network node 150. In some embodiments, the circuitry and elements of NMD 102 may be comprised within at least one of a noise dosimeter, sound level meters, hearing protection devices (hpd), non-attenuating headsets, or any combination thereof. NMD 102 may be configured with capabilities for noise monitoring and mapping, sound exposure monitoring, passive sound attenuation, active sound attenuation, leakage control, hear-through, and communication/entertainment, featuring passive sealing, electro-acoustic transducers, electric circuitry, and in some embodiments, hearing protection elements.

Figure 3A:
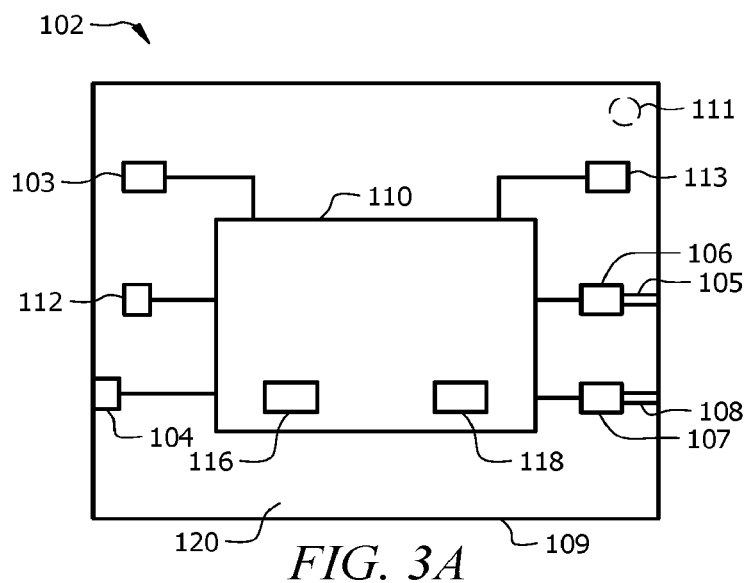
FIG. 3A is a block diagram of a noise mapping device having integrated noise monitoring and mapping according to an example embodiment.
Figure 3B:
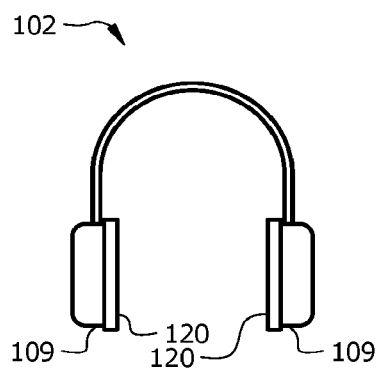
FIG. 3B is an illustration of a housing and hearing protection elements for the noise monitoring device of FIG. 3A according to an example embodiment.
Figure 3D:
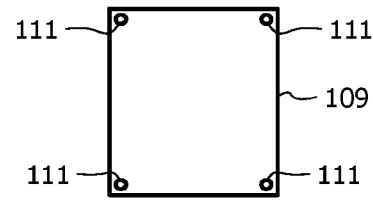
FIG. 3D is an illustration of a housing for the noise monitoring device of FIG. 3A according to an example embodiment.
Figure 3C:
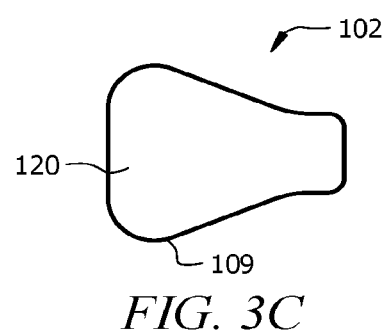
FIG. 3C is an illustration of a housing and hearing protection elements for the noise mapping and monitoring device of FIG. 3A according to another example embodiment.

As illustrated according to an embodiment in FIG. 3A, noise mapping device 102 comprises a noise map circuit 110 retained within an outer structure or housing 109. In some embodiments, the outer housing 109 may be worn by a user (e.g., the housing 109 being in the configuration of an ear piece or ear plug that each have hearing protection elements). NMD 102 includes at least one outer microphone 104 and at least one speaker 107. The sound inlet of the outer microphone 104 may be mounted to the outer structure 109 and configured to receive external noise and sounds from the environment. The outer microphone 104 is electrically coupled to circuit 110, which is powered by power source 112 (e.g., a rechargeable battery, a disposable battery, and/or an AC power supply). The NMD 102 may transmit audible sounds from speaker 107 via acoustic channel 108. In some embodiments, NMD 102 includes a second microphone 106, which may be disposed on an inner portion of the housing 109 that is facing the ear of a user. The second microphone 106 receives sound via noise channel 105. The circuit 110 may be configured to assess sound exposure based on the signals from the microphones 104 and 106, and store received sound data on memory in circuit 110. The NMD 102 comprises a radio transceiver (e.g., transceiver configured for wireless communication via cellular frequencies, WiFi, Bluetooth, RFID, etc.) that sends and receives information to and from an external computer system (e.g., computer system 160 of FIG. 1). In some embodiments, NMD 102 comprises a user interface 113 that is operable to display information pertaining to the measured noise. For example, interface 113 may receive commands from circuit 110 to power one of a red, yellow, or green exposure light (e.g., LED bulb or color on LED display). The circuit 110 may also be configured to provide audio alerts (via speaker 107) to users regarding sound exposure status and/or instructions to begin wearing hearing protection, switch to a type of hearing protection that has a higher NRR rating, directions to the location of the nearest hearing protection dispenser (e.g., dispenser 140). Various audio alerts may be provided as the wearer approaches different levels of sound exposure as calculated using the noise map and sound data received from various NMD's 102, such as transitions between low and medium and between medium and high exposures in each ear (e.g., sending an audio alert when predefined exposure or sound level thresholds (dB) are exceeded). In some embodiments, the circuit 110 may generate an audible dialog to the user indicating noise exposure, directions to avoid noise exposure, directions towards the nearest dispenser 140, and/or may further provide electronic signal tones representative of noise exposure level.

In some embodiments, a NMD 102 may provide hearing protection via hearing protection element(s) 120 that are configured to support active and/or passive noise cancellation and may be configured to provide hear-through capabilities. This may be because in some embodiments, NMD 102 is worn by a user during their work shift. For example, regarding hear-through capabilities, the sound captured by the outer microphone 104 may be converted to digital signals and provided to a processor of circuit 110. The processor may filter the external sound detected by the outer microphone 104 (by filtering the signal to ensure that sounds are only reproduced at a safe level) and direct the speaker 107 to generate the filtered sounds within the user's ear (thereby allowing hear-through capabilities). In other embodiments, such hear-through could be analog.

Regarding active noise cancellation, a microphone (e.g., outer microphone 104) is positioned on housing 109 to measure ambient noise. Microphone 104 in one embodiment is positioned on an outside portion of the housing 109. A separate microphone (e.g., inner microphone 106) may be located inside housing 109 (e.g., inside the earpiece and/or earplug illustrated in FIGS. 3B, 3C) and is disposed within the housing 109 to measure sound that the user's ear is exposed to after noise cancellation is performed. The measured noise from the environment (received via outer microphone 104 and inner microphone 106) may be converted to digital signals and provided to a processor of circuit 110 (although in other embodiments, active noise reduction could be analog). The circuit 110 performs noise cancellation calculations and provides a noise cancelling signal to a speaker 107 positioned to transmit cancelling noise sounds into the ear via channel 108. Algorithms for active noise cancellation and control are generally known and thus will not be described in detail herein, but may include active noise cancelling feedback of acoustic signals converted by at least one of the microphones (e.g., 104 and/or 106) through the speaker 107. In some embodiments, the transceiver 103 may receive a noise cancellation settings package (which is associated with hearing protection) that is specifically created for a user associated with NMD 102. The amount of noise cancellation (e.g., range of noise cancellation signals produced and transmitted via speaker 107) may be adjusted (e.g., increased and/or decreased) by circuit 110 implementing the noise cancellation settings package. In some embodiments, the amount of hearing protection provided to a user may be activated, adjusted if already activated, and/or deactivated based on saving the noise cancellation settings package to memory of circuit 110. In some embodiments, such as illustrated as ear pieces and ear plugs in FIGS. 3B and 3C, the housing 109 may include the same microphones 104, 106, circuit 110, and speaker(s) 107 such that noise cancelling and hearing protection is provided to both ears of a user. When configured as a passive hearing protection device, NMD 102 may not provide active noise cancellation via speaker 107, but still have noise attenuation material (e.g., noise protection element 120) that decreases the amount of external sound reaching the user's ear.

In some embodiments, a plurality of NMD's 102 are stationary in location at a work site, such as within the defined area 190 in system 100 of FIG. 1. Put simply, stationary NMD's 102 may be attached at certain, known locations within a work site so that their geo-coordinates (e.g., location) are fixed relative to other portable NMD's that are worn by a user. In embodiments where an NMD 102 is configured to be stationary, the housing 109 may optionally be mounted to a surface via an attachment anchor 111 (e.g., clips, fasteners, harness). The attachment anchor 111 may be implemented to keep housing 109 in a fixed, anchored position (e.g., at a defined location that is stationary and known to the NMD 102 and computer system 160 based on the coordinates of the NMD 102 not changing over a defined time period).

Figure 4:
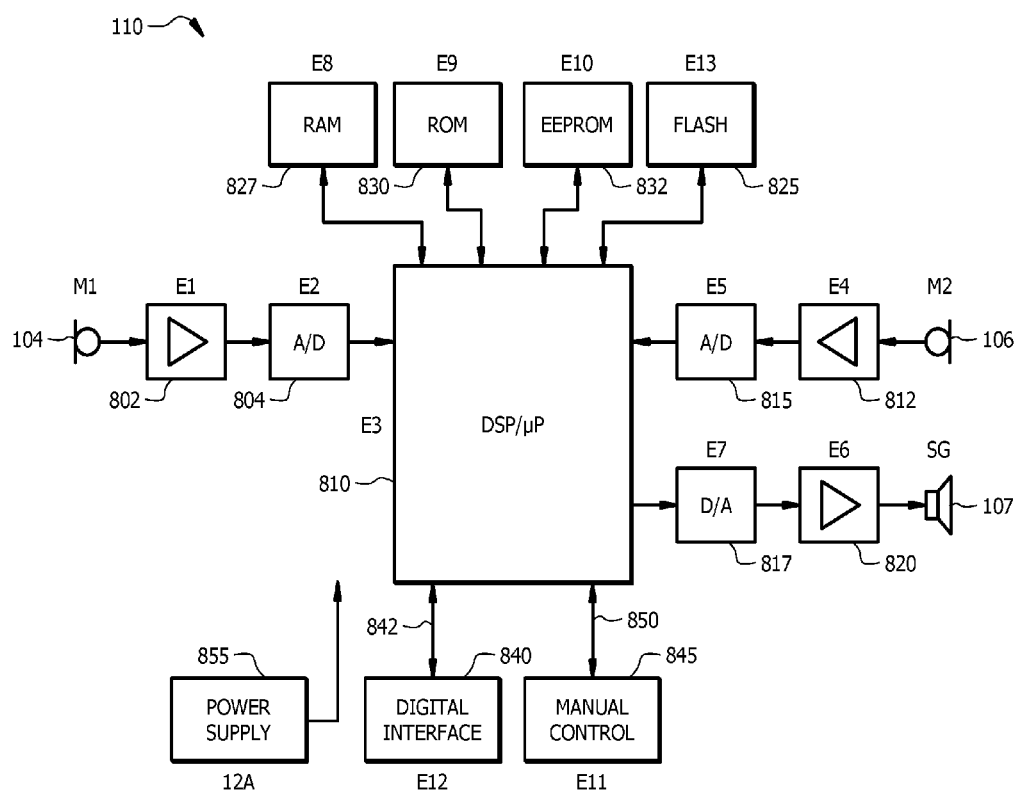
FIG. 4 is a block diagram of circuits utilized to perform noise monitoring and mapping according to an example embodiment.

Irrespective of the configuration of housing 109 and whether the NMD 102 is worn by a user or remains stationary (e.g., fixed position), the NMD 102 comprises circuit 110, which has an application 116 and locator unit 118 (although for fixed NMD, the locator unit function could be by providing location data to the computer/fixed NMD unit during the commissioning phase (such that the locator unit for such fixed NMD would basically be data provided to/stored within (e.g., a database/memory accessible by) the computer or fixed NMD unit), and/or in other embodiments the physical locator unit for fixed NMD could be optional). In some embodiments, the transceiver 103 may include a global positioning system (GPS) device that sends GPS signals to locator unit 118 stored within circuit 110. The application 116 and locator unit 118 may be stored in memory of circuit 110 and execute via one or more processors. The locator unit configures circuit 110, upon execution, to receive location information, determine a position (e.g., location) of the NMD 102 and for output a corresponding location data. The locator unit 118 may be provided with location information from transceiver 103 based on received GPS signals, wireless local area network (WLAN) and/or cellular signals received from network node(s) 150, and/or Bluetooth signals using trilateration or fingerprinting methods to determine a geographical position. The circuit 110 may comprise electric circuitry as shown in FIG. 4, which may be configured and/or programmed to achieve several possible functions. By way of example, in an embodiment the outer microphone M1 104 may pick up ambient (external) sound (e.g., sounds received from one or more noise sources 154 in FIG. 1). A signal from the outer microphone M1 104 may be amplified via amplifier E1 802 and then sampled and digitized in an analog-to-digital converter E2 804. The signal may then be fed to a processing unit E3 810 that may be one or more digital signal processor (DSP), a microprocessor, or a combination of the two. In some embodiments involving active noise cancellation, a signal from the inner microphone M2 106, which picks up sound in the user's ear between the hearing protection element 120 and the user's eardrum, may be amplified via amplifier E4 812, then sampled and digitized in the analog-to-digital converter E5 815, and then fed to the processing unit E3 810. The processor 810 may generate a digital signal for noise cancellation and/or to provide instructions or a warning tone to the user via execution of application 116 (which is stored in one of the memory elements discussed below). Once generated in the processing unit E3 810, the output signal is converted to analog form in the digital-to-analog converter E7 817 and fed to the analog output amplifier E6 820 that drives the speaker 107. In some embodiments, the output sound signal produced by the speaker SG 107 is fed to the user's eardrum (tympanum) via channel 108. In embodiments where the user is not swearing the NMD 102 over and/or in their ear, the speaker 107 may generate an output sound, tone, and/or instruction within the defined area 190 so that a user may be alerted to the potentially hazardous noise event.

The processing unit E3 810, in this embodiment, is connected to memory elements such as flash memory E13 825, (random access memory) E8 827, ROM (read only memory) E9 830, and EEPROM (electronically erasable programmable read only memory) E10 832. The memories or computer readable storage devices E8, E9, E10, and E13 are used for storing computer programs (e.g., application 116 and locator unit 118) used to cause a processor 810 to perform algorithms such as noise cancellation, sound exposure calculations, noise mapping data. (e.g., received sound level data and location data), instructions and/or tones for alerting the user via speaker 107, or any other audible dialog or sound commanded by the computer system 160 and/or other NMD's 102. The storage devices may also store one or more of, filter coefficients, test responses, test results, sound exposure data, analysis data, location data, and/or other relevant data.

The circuit 110 may allow for each NMD 102 to be connected to other NMD's via interface E12 840 (which may be via wireless transmission through a digital radio link represented at 842 coupled to transceiver 103, such as via a Bluetooth standard, WiFi protocol, cellular technology, etc.). A manual control signal may be generated in E11 845 and fed to the processing unit E3 810 via connection 850. The control signal may be generated using a user interface (e.g., interface 113) via buttons, switches, touchscreen etc. and may be used to turn the unit on and off, to change operation mode, to signal responses, or input commands. When a user inputs commands via the interface 113, the specific input (e.g., via certain buttons and/or in response to touchscreen input) may be individually assigned to generate these control signals, or may control one or more different functions depending on different modes of operation. In an alternative embodiment, a predetermined voice signal from the user may serve as one or more control signals and picked up by one of the microphones 104, 106. The circuit 110 may be powered by power source 112 via the power supply 855 (e.g., via a primary or rechargeable battery arranged in the ear terminal or in a separate unit, or may be an electrical power connection).

The application 116 that executed on circuit 110 detects and determines environmental noise on a geographical (e.g., location) basis. In addition, the circuit 110 may determine individual noise patterns to which a specific user is exposed (e.g., a worker associated with a user identifier stored in datastore 156, which may be mapped to noise mapping device 102 upon being checked in/out by the worker when their work shift begins/ends. The noise data sent to the noise map application 166 of computer system 160 may include the time or the period of the noise recording in the defined area 190. When analyzed in combination with the sound level value, the noise data provides a measurement of intensity for the environmental sound as it corresponded with the time of day. This allows for calculation of the average and/or overall noise exposure amount for the user over a defined period while in the defined area 190. In some embodiments, the circuit 110 may compare the received noise signals (from one of the microphones 104, 106) with a stored noise distribution list of known environment sounds and/or noise levels (e.g., a list stored in memory of the circuit 110 that comprises threshold values, measured in dB) thereby allowing for circuit 110 to assess whether the environmental sounds are industrial, work, machine, or road noise, or whether the environmental sounds correspond with normal speech that may not be hazardous to human ears.

The circuit 110 may reduce consumption of power from power source 112 (e.g., a battery) by only storing and transmitting noise data having certain noise values, such as when the received sound signals exceed at least one stored thresholds. For example, when the received noise signals are in excess of 80 dB and continue for ten seconds, the circuit 110 determines that a threshold (stored in memory) is exceeded, and the received signal is converted into noise data for transmission to the computer system 160. In some embodiments, the circuit 110 may determine that power source 112 is not a battery, but instead corresponds with a power supply via connection with a wall outlet. When not running on battery power, the circuit 110 (via execution of application 116) may generate noise data irrespective of whether the received noise signals (from the microphones 104, 106) exceed a threshold (e.g., exceed stored sound level (e.g., dB values)). In some embodiments, the circuit 110 may use locator unit 118 to broadcast its location to other noise mapping device 102 that are proximately located (e.g., within a distance that allows a transceiver of a noise mapping device to receive the broadcast). In some embodiments, the circuit 110 broadcasts its location (and in some embodiments also broadcasts its detected noise data) (e.g., sends a packet comprising geolocation coordinates and an identifier of the noise mapping device) when it is not running off of a power source 112 that is depletable when it is running off a wall unit instead of a battery that can be drained of its stored power). For example, when not running off a battery, the noise mapping device may locally broadcast a packet comprising geolocation coordinates, an identifier of itself, and noise data spanning a defined time period. Local broadcasting may be accomplished via Bluetooth and/or short-range WiFi broadcasting, such that other noise mapping devices may receive the broadcasted information when they are within a defined distance (e.g., ten meters) of the device doing the broadcasting.

In some embodiments, the NMD 102 measures noise levels as a time-averaged value. For example, a time-averaged value may be the time average sound level and may be colloquially referred to as the "equivalent continuous sound level" (which hereinafter may be referenced as $L_{AT}$ which may comprise LAeq,T (e.g., A for A-weighted level, eq for equivalent and T for time duration—so for example, LAeq,8 h for an eight hour equivalent level)), which is detected and determined (e.g., by NMD 102 and/or computer system 160). The equivalent continuous sound level may be included in the noise data sent from the NMD 102 to the computer system 160.

Figure 2:
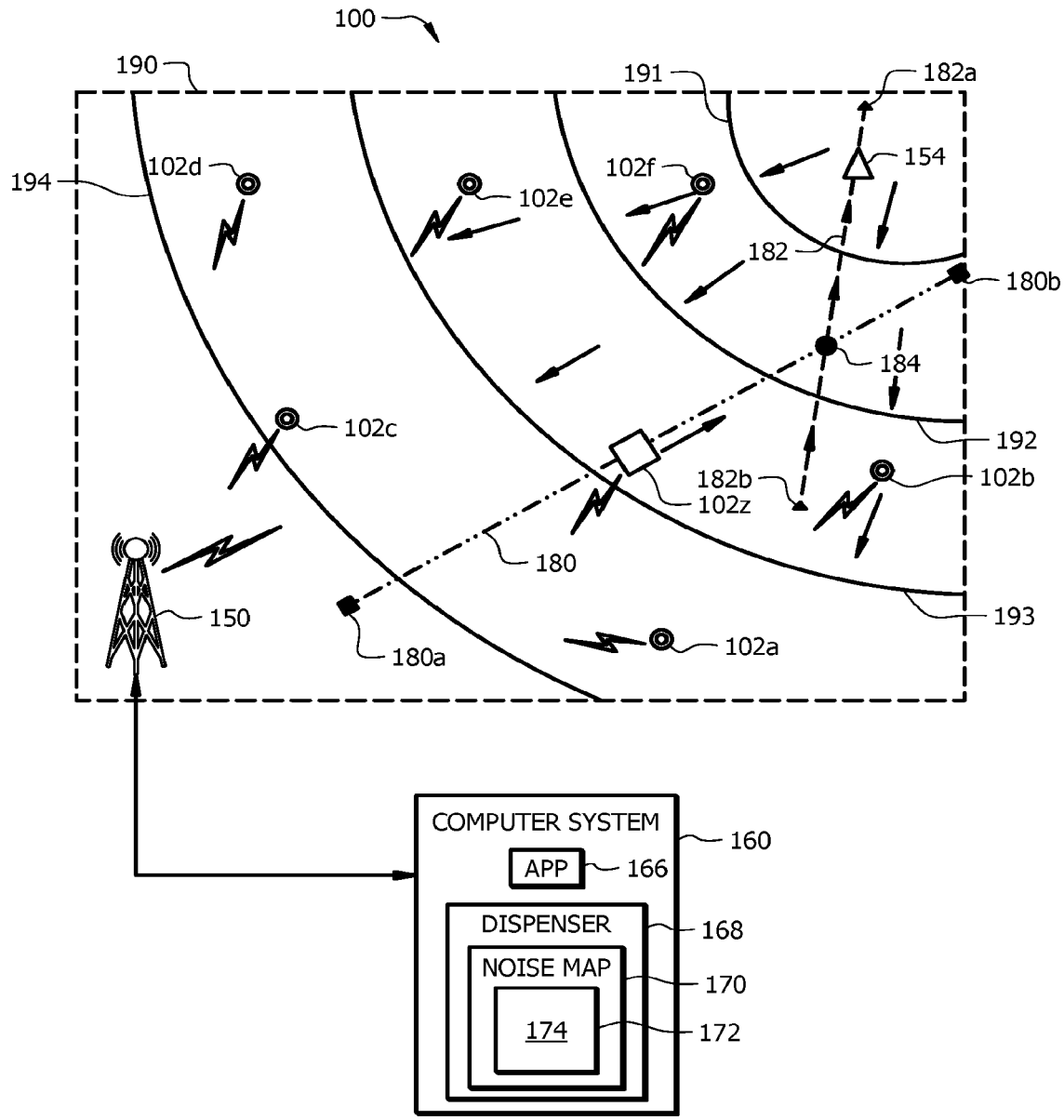
FIG. 2 is a block diagram of a noise mapping and monitoring system in accordance with an illustrated embodiment shown in FIG. 1.

Continuing with discussion of FIG. 1 with reference to FIG. 2, the system 100 includes computer system 160 that generates a noise map 170. FIG. 2 illustrates an embodiment of a dynamic and real-time noise map 170 that is created via computer system 160 for display (locally and/or remotely) on display 168. Application 166 executes on computer system 160 receives noise data (comprising noise level values and location information) from a plurality of NMD's 102a-102z to create a noise distribution map (referred to as noise map) 170 across a predetermined area 190. In the embodiment illustrated in FIG. 2, some of the noise mapping devices may be configured to be stationary (e.g., with fixed geolocations within predefined area 190) and at least one noise mapping device is portable (e.g., wearable by a user and/or attached to equipment that moves about the predefined area 190 and changes geolocation). For example, as illustrated in FIG. 2, the predefined area of system 100 may comprise NMD's 102a-102f that are stationary such that they each correspond to a location that does not change over a defined time period. The defined area 190 may also comprise NMD 102z, where NMD 102z is not stationary and is configured to be portable with changing location information (e.g., when worn by personnel moving about the area 190). For example, in some embodiments, the NMD 102z may be configured with a housing 109 and hearing protection element 120 as a hearing protection headset capable of active noise cancellation. In another embodiment, the NMD 102z may be portable, but not have hearing protection elements that allow for passive and/or active noise cancellation.

As the worker wearing the NMD 102z moves from origin location 180a towards a target location 180b within the area 190, the NMD 102z may receive noise signals and determine location information while moving between the locations. The circuit 110 of NMD 102z may create noise data that comprises at least a combination of the sounds measurements and the location information (multiple geolocation coordinates) and include the noise data in a packet, which the NMD 102z wirelessly transmits application 166 via one or more network nodes 150. Although stationary, each of the NMD's 102a-102f may perform the same functions as the moving NMD 102z, and thus, each 102a-102f may independently measure sounds, determine its location (such as by either pulling from memory or comparing with a last known location coordinate), and transmit the packet to application 166 of computer system 160. Each NMD 102a-102z may append an identifier to the packet, where the identifier corresponds with a unique identification of the noise mapping device, which the computer system 160 uses to determine which received packets belong to each NMD 102a-102z.

In some embodiments, one or more NMD's 102a-102z may determine their current location within area 190 via GPS signals or by trilateration using multiple network nodes 150. However, there may be a certain allowable error in determining the exact location, due to the sensitivity of GPS and/or radio transceiver interface. Thus, to improve location accuracy, in some embodiments, the location information determined by one NMD may be supplemented with information collected from another NMD. For example, NMD 102z may send a probe message requesting a response message from one or more NMD's 102a-102f (via transceiver(s) 103 of each NMD). The NMD 102z receives, collects, and measures (or derives from responses (e.g., via MAC addresses) the parameters of wireless signals transmitted by the transceivers of other NMD's (e.g., from one or more of NMD 102a-f). The signal parameter measured by the receiving NMD (e.g., NMD 102z receiving signals from one or more of the stationary NMD's 102a-102f may be any appropriate indicator of distance (e.g., received signal strength indicator (RSSI), time of flight, etc.). Based upon the measured signal parameters, the NMD 102z may determine the stationary NMD (e.g., one of the NMD's 102a-102j) with the best measured signal parameter (e.g., the greatest relative RSSI if RSSI is used, the shortest relative time-of-flight if time-of-flight is used, etc.), and store the unique identifier corresponding to the NMD that had the best measured signal parameter (e.g., NMD 102z determining that NMD 102a has the best measured signal parameter and thus NMD 102z stores the unique identifier of NMD 102a for later use when transmitting to computer system 160).

In some embodiments, once the NMD 102z determines its own location information and receives the identifier from the other NMD that had the best measured signal parameter (e.g., NMD 102a), the circuit 110 of NMD 102z creates and/or includes at least four portions of information in noise data that is sent to the mapping application 166 executing on computer system 160. The four portions of the noise data may include 1) the values of measured sound level determined from the received signals (via microphone(s) 2) the location information determined by circuit 110, 3) the NMD's own identifier (e.g., NMD 102z from the above example), and 4) the identifier and signal measurements from the other NMD that had the best measured signal parameter (e.g., NMD 102a from the above example). The circuit 110 may then transmit the noise data (comprising the four portions) to mapping application 166 of computer system 160 via network node 150.

Upon receipt of the packet, the application 166 executing on computer system 160 saves the noise data (e.g., in memory 164 and/or datastore 156) and attempts to determine location of the NMD 102 that sent the information (e.g., in this example, NMD 102z). If only location information from the NMD 102z is included in the noise data, then application 166 may extract the geolocation coordinates from the noise data and plot them according to x and y coordinates against a digital blueprint corresponding to the predefined area 190 (e.g., pulling a digital blue print from datastore 156 and overlaying the geolocation coordinates on the digital blueprint). In some embodiments, the digital blue print may be an electronic map file that corresponds with the predefined area 190 known to computer system 160. In embodiments where the NMD 102 sends noise data that comprises information from other devices (e.g., NMD 102z sending noise data with identification and signal parameters pertaining to NMD 102a), the application 166 may verify the accuracy of the location of NMD 102 (e.g., NMD 102z in the above example). In order to determine how accurate the location information is that was determined by NMD 102z, the mapping application 166 extracts the signal parameter measurements and identifier from the noise data, and estimates a location of the NMD 102z based upon the signal measurements.

If the signal measurement is based upon RSSI then the assumption upon which the estimate is based is that the signal attenuates in a manner that is proportionate to distance. By knowing the amplitude of the transmitted signal and amplitude measured by the NMD 102z, the application 166 can calculate a distance from the NMD 102z to each of the other noise mapping devices (e.g., 102a-102f which are stationary and have geolocations known to the application 166). By knowing the distance from the NMD 102z to each of the other NMD's 102a-102f, the application 166 triangulates the position of the NMD 102z by determining the intersection of the distances from each of the other NMD's 102a-102f to the NMD 102z. If the signal measurement is based upon time of flight, then a similar process is used. In this case, the application 166 determines distance based upon the time of flight of the signal from the NMD 102z to each of the other NMD's 102a 102f and triangulates in the same manner.

Irrespective of verifying and determining the location of NMD 102z using time of flight and/or RSSI, the application 166 may also compare the estimated location of the NMD 102z with the known location of other NMD's 102a-102f to obtain a location error measurement or value. By this, the application 166 may perform the initial determination of location for NMD 102z when first creating the noise map 170, and thereafter may refresh the map dynamically, with new location information, and append the information with the location error measurement or value. This may improve the processing efficiency of the computer system 160, while also improving the battery life of the NMD 102z due to the NMD 102z not having to constantly probe other NMD's (e.g., 102a-102f) each time noise data is sent, but rather may be performed once or periodically.

The location error measurement or value may be monitored over a period of time to detect a gradual or rapid degradation of location accuracy. Once the degradation exceeds a defined threshold value stored in datastore 156, the application 166 may push an alert message to display 168 and/or record the event in a log stored in datastore 156. This noise measurement and location mapping information and reporting processes may be performed by each NMD 102 (e.g., each NMD 102a-102z). In doing so, the application 166 obtains a location error measurement value for each of the NMD's 102a-102z. The location error measurements may be used as a correction factor to correct the estimated locations of the NMD's 102a-102z. The application 166 may adjust its location estimate for a specific NMD 102 (e.g., one of NMD's 102a-102z) by taking into consideration the location errors for several neighboring NMD's.

The application 166 provides display 168 with a generated noise map 170, such that a predefined area 190 is depicted on the noise map 170, such as illustrated in FIG. 2. Included on the noise map 170 may be a designated location of each of the stationary NMD's 102a-102f and the moving NMD 102z, where NMD 102z is centered at location 174 in the noise map 170.

Shown on the display 168 around the location 174 of the moving NMD 102z may be a bounding box 172 that indicates the estimated location error of the NMD 102z. For example, if the location error of the other stationary NMD's 102a-102f (closest to the estimated location of the moving NMD 102z) indicates an error of two feet, then the bounding box 172 may be shown around the NMD 102z with sides having at least a length of two feet. Since the error is a vector including x and y components, it is also possible to have a bounding rectangle 172 in which the length of sides are at least the corresponding x and y amounts. However, the bounding box 172 may not be exactly the size of the error measurements as there may be other sources of error that should be considered and that may suggest that the box 172 be larger. Further, rather than a rectangle, the error may be indicated as an area surrounding the estimated location where the shape and size of the area may be proportional to the error vector.

With the noise map 170 created, application 166 may determine a trajectory 180 along which NMD 102z is traveling based on the location of the NMD 102z, locations of the other NMD's 102a-102f and origin location 180a that is pulled from historical noise data and location information previously sent to the application 166. From this, the application 166 identifies a target location 180b corresponding to the direction NMD 102z is moving towards, and then creates a trajectory line (or path) 180 for display on noise map 170. The application 166 also extracts the noise values from the noise data received by each NMD 102 (e.g., 102a-102z). Based on the sound level values sent from each NMD 102 within the defined area 190, the determined locations of the NMD's 102a-102z, the application 166 determines concentrations of noise levels and determines a location of the noise source 154. For example, the application 166 may use the noise data received from NMD's 102a-102z to determine that the sound level values from NMD 102f are the highest, with sound level values from NMD's 102e, 102b, and 102z being next highest (as measured in sound pressure levels (e.g., dB values)). The application 166 may assign and display zones of noise intensity on the noise map 170, and in some embodiments, may include a different color in each zone. For example, application 166 may define a first zone 191 to be within a first defined distance from noise source 154 (e.g., within 10 feet of noise source 154), a second zone 192 to be within a second defined distance of noise source 154 (e.g., within 20 feet of noise source 154), a third zone 193 to be within a third defined distance of noise source 154 (within 30 feet of noise source 154), and a fourth zone 194 to be within a fourth defined distance of noise source 154 (within 40 feet of noise source 154). In some embodiments, the application 166 may provide each zone with a color intensity that matches the intensity of sound produced by the noise source, where sound levels below 50 dB are colored in green (e.g., fourth zone 194), sound levels between 50-80 dB colored in yellow (e.g., third zone 193), sound levels between 80-100 dB colored in red (e.g., second zone 192) and sound levels greater than 100 dB colored in brown (e.g., first zone 191).

As the sound level values received from the NMD's 102a-102z change, the application 166 determine an noise origin 182a of noise source 154 and the current position of noise source 154. The application 166 determines a target noise endpoint 182b and creates a noise source trajectory 182 based on the noise data (comprising noise values and location information) from each of the NMD's 102a-102f and the determined location of the noise source 154. In some embodiments, the application 166 may detect that NMD 102z will be in danger of being within a hazardous noise zone (e.g., the first zone 191 and/or second zone 192) due to the trajectory 180 of the NMD 102z and the trajectory 182 of noise source 154 intersecting at intersection location 184. In some embodiments, the application 166 may determine the distance from the intersection point 184 to the NMD's 102z current location, and after finding the average velocity of NMD 102z based on the measured noise data from NMD 102z, the application 166 determines the estimated time left before NMD 102z is in danger of incurring a hazardous noise event (e.g., being exposed to sound levels above a defined (dB) value stored in datastore 156, such as 80 dB). In some embodiments, the application 166 may push the noise map 170 to one or more displays 168, which may be accessible for view by the user wearing NMD 102z. In some embodiments, application 166 pushes an alert to NMD 102z with that presents an audio, visual, and/or haptic warning to the user of NMD 102z. For example, application 166 may warn NMD 102z that it is heading into a zone that is producing hazardous noise.

In some embodiments, the application 166 may use the identifier of NMD 102z to access datastore 156 and identify the user currently assigned to the NMD 102z. The application 166 may determine the level of hearing protection associated with the user currently using NMD 102z, such as determining that the user should not be exposed to sound levels above 80 dB. The computer system 160 uses application 166 to obtain settings information corresponding to the amount of hearing protection for the user. For example, if the application 166 determines that NMD 102z provides hearing protection via hearing protection elements and active noise cancellation (e.g., hearing protection elements that are configured around the ear and have circuitry 110 that provides active noise cancellation), then the application 166 may push the settings information to the NMD 102z, where the settings information comprises a threshold value for the allowable sound level of the user. The NMD 102z may receive the settings information and update an existing threshold value with the new threshold value from the received settings information. This may allow circuit 110 of NMD 102z to provide active noise cancellation so that sounds heard by the user will be mitigated to below the threshold level (e.g., below 80 dB).

In some embodiments, the application 166 may determine that NMD 102z may not have adequate hearing protection capabilities (e.g., not having active noise cancellation capabilities and/or the hearing protection elements do not provide a high enough NRR value for the user). For example, if (in an embodiment) the NMD 102z is a hear-through device, the application 166 may push an alert to NMD 102z, which upon receipt, provides instructions via the speaker of NMD to head towards the nearest hearing protection dispenser 140. As the user is walking towards the dispenser 140 based on the directions sent by the application 166, the application 166 may also send a release message to dispenser 140 via network node 150, where the release message commands the dispenser 140 to provide the user wearing the NMD 102z with a hearing protection device 142 (e.g., an set of ear plugs and/or ear muffs).

(A) Regarding a Moving Noise Source that is a Potential Hazard

In some instances, the computer system might determine from noise data (e.g., the noise data sent from each of the communicatively coupled NMDs) if there is a moving noise source. For example, this might be accomplished in some embodiments by identifying the characteristics of the sound, cross-referencing the location information of the various noise monitoring devices (e.g., which detect such sound characteristics) with the external sound level that the devices pick up from the identified sound source, and using the difference level from various noise monitoring devices to identify/determine the path (and/or speed) of the moving noise source. In some embodiments, the computer system might compare the sounds levels from the detected noise data with sounds levels stored in a database, and based on the comparison, determine what is the cause of the moving noise source (e.g., the identification of the vehicle or other moving machinery that may likely be the cause of the moving noise). The computer system may project a trajectory or anticipated course of movement for the moving noise source (which may be presented on a display in communication with the computer). The computer might then determine if any NMDs are located along the trajectory of the moving noise source and send a warning to any such NMD along the trajectory (so that the user can be aware of a possible physical danger that they might not hear due to wearing of the NMD). Optionally, the computer might also consider movement (e.g., trajectory) of the various other NMDs in the area so that the computer may determine if one or more NMD is likely to intercept the trajectory of the moving noise source (such that a warning might be sent to each NMD that is affected). In other words, in some embodiments, the computer might account for both the trajectory of the NMD and the trajectory of the moving noise source to determine if a warning (regarding a potential physical hazard to the user of the NMD) should be sent to any specific NMD. The warning sent to the NMD might comprise one or more of the following: a sound beacon/tone/beeping, that varies in volume based on proximity to moving noise source (e.g., volume increases as moving noise source approaches the NMD); adjustment of hear-through settings (so user is more likely to hear moving noise source instead of another electronic communication, thereby allowing the user to avoid interception with the noise source); activating a vibration (e.g., via a vibration unit not shown) that varies in intensity based on proximity to moving noise source; change to tactility of a user interface on the NMD; three dimensional audio; and/or activation of a light that varies in intensity as the NMD gets closer to the moving noise source.

(B) Regarding Sharing of a Detected Alarm Between Devices

In some instances, the computer might use the generated noise map to detect an alarm based on one or more areas of the noise map corresponding to a higher sounds level than others and/or a specific frequency of sound not normally associated with that zone/area. So for example, if the sound levels are above a certain threshold, such as multiple noise sources each producing sounds above 90 dB and/or an alarm of a certain frequency sounding (e.g., via broadcast speakers, for example of a PA system), then the computer system may instruct NMD's in the area to activate noise cancelling (if possible), warn certain NMDs that other NMD's have detected potentially hazardous noise levels in the area (e.g., in proximity or abutting the alarm zone), direct one or NMD's toward a hearing protection dispenser location, and/or alert the user of all noise monitoring devices in the area/zone and/or adjacent areas/zones and/or moving towards such areas/zones. This type of advanced alarm detection may help to provide for advanced notification to users/workers in an affected zone who might not otherwise hear the high sound levels (or alarm broadcast via a speaker in the room) due to the hearing protection that they are wearing (e.g., a NMD with hearing protection elements). The computer system might further be configured to detect if a NMD is (in an adjacent zone and) moving towards the alarm zone (based on trajectory of NMD's movement via use of location data over time) and transmit a warning (e.g., pre-alarm) to such NMD. In other words, the computer could use the detection of an alarm in a zone, in conjunction with the movement trajectory information about specific NMD outside the zone (for example in adjacent zones) to send either an alarm or a lesser warning to additional NMD's which might be outside the affected zone but which still might benefit from knowing about the alarm in a particular zone. In this way, additional workers might be protected and/or steered clear of potentially dangerous zones (e.g., essentially providing an earlier warning system to those outside the affected zone).

(C) Regarding Comparing Location of a User's NMD in the Noise Map to the Specific Individualized Hearing Threshold for that User In yet other instances, the NMD might be associated with a user (e.g., via the user checking out the NMD by swiping an RFID tag with the worker's identifier, which is then sent to the computer system and the computer associates the worker's identifier with one of the identifiers corresponding, to the NMD they are checking out, or otherwise by associating the noise monitoring device serial number and user ID, for example within a database), and the computer might further be coupled to a database storing individual user hearing test data and settings (e.g., thresholds and/or exposure tolerance corresponding to sound levels for a user, measured in dB, which may be lower than the standard threshold). Then, the computer may correlate user's NMD location with noise level (via the noise data and location on the noise map) and compare to the database to determine (in an individualized way) if a warning, should be sent to a specific user's NMD (for example, if the specific user wearing the NMD is more sensitive and should not be exposed to such loud noise and/or such frequency of noise, then the computer system may send a warning to that user's NMD before other NMDs in the area). The computer could then transmit a warning to the specific user's NMD recommending, movement to another zone based on the noise map (e.g., in relation to the user's individualized threshold information and location on the nose map). Additionally (similar to the discussion above about accounting for the movement/ trajectory of specific NMD), the computer might also detect if a NMD is (in an adjacent zone and) moving towards the zone having noise in excess of the user's threshold (based on trajectory of NMD movement based on location data over time in comparison to the noise map) and transmit a warning (e.g., recommendation) to such NMD (e.g., regarding the amount of time the user might spend in that zone and/or an alternative zone better suited to the user).

(D) Regarding Movement of One or More NMDs Towards a Potential Noise Danger Zone Additionally (similar to the discussion above about accounting for the movement/trajectory of specific NMD), the computer might also detect if a NMD is (in an adjacent zone and) moving towards a noise danger zone (e.g., a predefined distance from a noise source such that sounds within the zone are measurable to be above a defined sound level, such as 100 dB), for example having noise in excess of the user's threshold or over a certain sound pressure (e.g., dB) level (based on trajectory of NMD movement based on location data over time in comparison to the noise map) and transmit a warning (e.g., recommendation) to such NMD (e.g., regarding the amount of time the user might spend in that zone and/or an alternative zone better suited to the user). This might be particularly useful if the user has a lower hearing threshold, such that certain zones should be avoided. Then, for example, the computer might access a database with the individual user information (as discussed above), and use that in conjunction with the noise map and the trajectory of the NMD for that user to issue a warning before a worker enters a zone which might damage his hearing (so that the user would not even enter such a dangerous noise zone).

(E) Regarding Suggesting or Dispensing Hearing Protection to Incoming Users Based on Noise Map Information for that User's Work Zone In some instances, the noise map might be used to help prepare an incoming worker for the specific conditions in the work zone (e.g., predefined area displayable on the noise map and corresponding to where the user works) they will be entering (e.g., using sensed noise data from within that zone from NMDs). So for example, for a new worker coming into a facility for which a noise map is currently being generated via NMDs already in the area, the computer might determine the zone (of the noise map) that the user will be entering (e.g., based on the user checking out a NMD and the computer tracking the movement of the user via the NMD's transmitted location information) and suggest/recommend or provide (e.g., automatically dispense) appropriate hearing protection device to that worker (based on the noise map) before the worker enters a dangerous zone (e.g., dispensing ear plugs for the user to wear). In some instances, the user's specific hearing information/threshold might also be considered when determining the appropriate hpd for that specific user in the specific work zone (e.g., updating a NMD with settings information that updates noise cancellation thresholds for the user's NMD as discussed above). The computer could also determine/estimate the appropriate amount of time that an incoming user with a specific type of hearing protection can safely spend in the work zone (e.g., wearing a NMD that is configured with hearing protection elements and/or wearing hearing protection separately from the NMD worn by the user), and for example, notify the incoming worker up front or provide a signal warning of the expiration of such estimated time and the need for the worker to move out of the zone.

(F) Regarding Checking Hearing Protection Level vs. Sounds in the Noise Map to Determine Adequacy of Hearing Protection In some instances, the computer might compare information for the location and type of NMD the user is wearing with noises and zones on the noise map, which in turn allows the computer to determine if the user has sufficient hearing protection in place, and if not (e.g., the user's NMD not having hearing portion elements (such as being configured as an ear plug or ear muffs) or the user's hearing protection device not having a high enough NRR to protect against the noise levels in the zone, thus considering the user's hearing protection to be insufficient/inadequate), and to transmit a warning to the user's NMD if the user's type of hearing protection is found to be inadequate. In some instances, the user's individual NMD may determine if the hearing protection provided by that NMD is adequate (e.g., in the same manner discussed for the computer), and if not, the user's NMD may announce a warning to the user before receiving instructions from the central computer system to do so. The pooled noise data of the data map might also be analyzed (e.g., by computer) to determine over time if hearing protection procurement for a facility and/or a zone/area within a facility should be altered (for example, if more protective hearing protection is needed, based on the collected noise exposure over time). In some instances, each NMD may compare received noise levels with the noise level presented on the noise map in order to serve as a check (e.g., verification) for whether the user's NMD is detecting noise correctly and thus detect possible malfunctions which may be reported to the computer system. If the sound values compared by the NMD using the noise map do not correlate, the NMD may determine that a malfunction exists, and thus send a message to the computer system indicating that data from the noise map data is inconsistent with the noise levels detected by the NMD. In response, the computer may send a notice message to the NMD, noting that the NMD should undergo maintenance, such as by restarting the power to the circuits or updating values stored in the memory of the NMD.

(G) Regarding Estimating Remaining Time User May Spend in Zone Based on Noise Map In some instances, the computer might generate an estimate of time to spend in the zone (based on location, type of NMD (e.g., whether the NMD is configured with hearing protection elements or not), noise map, and/or individual worker hearing info.) and transmit to the NMD. Such an estimate might also account for user's NMD movement or projected movement, to provide a better estimate of the time remaining for the user in the work area before the user exceeds a threshold for safe exposure to sounds. In some instances, the individual data from the NMD detecting noise could be compared to the noise map (which may include other displayed information), in order to serve as a check for whether the individual NMD is detecting noise correctly (e.g., to detect possible malfunction). If a possible malfunction is detected, then the estimate (of time remaining in the work area) might be calculated based on the time the user has already spent in the area and the data provided by the noise map, rather than relying solely on the individual NMD's detection of sounds. Further, a notice might be sent to the NMD, noting that it needs maintenance.

(H) Regarding Altering Configuration of NMD's that Provide Hearing Protection Based on Moving Noise Source Trajectory Info. from Noise Map In still other embodiments, the computer might use noise data (e.g., received from the NMD and used in the creation and display of the noise map) regarding a moving noise source to alter the set-up/configuration of one or more NMD's (that have hearing protection elements) and which are moving along a trajectory that may intersect the moving noise source. For example, the computer may alter/tune active noise cancellation (e.g., adjust the amount of noise cancellation to provide for more noise cancellation and thus hearing protection corresponding to a defined NRR) for any NMD that is configured with active noise cancellation and potentially will enter a hazardous zone while the moving noise source is traveling along its trajectory. The computer may receive noise data from one or more NMD in proximity to the moving noise source, determine if any other NMD are located along the trajectory (and/or within the zone) and that would need modification to better address that moving noise source to protect the user's hearing, and transmit a control signal to such NMD along the trajectory so that the noise cancellation settings are modifying on the NMD in advance of such NMD being in proximity to the moving noise source that would exceed a threshold for acceptable noise levels. As discussed above, the computer system may also detect if a NMD is moving towards the trajectory of the moving noise source (based on NMD's own trajectory calculated based on location information determined by the NMD over time) and alter the set-up/configuration of such NMD by activating noise cancellation and/or thresholds for noise cancellation. In other words, the configuration of the NMD (which has hearing protection elements) might be altered by taking into account the relative movement of the moving noise source relative to the NMD, to more finely tune the hearing protection functions of the NMD (for example, adjusting frequency ranges of an active noise cancellation filter of the NMD).

In some embodiments, the system might further comprise one or more fixed NMD's (e.g., NMD's that are not worn by the user but instead remain at a stationary position within a defined area of the noise map, which might include semi-fixed monitors installed for short duration for example). Each NMD that is stationary may comprise the same elements as NMDs which are portable (e.g., having a microphone, circuit, transceiver configured/operable to communicate with the computer). In some embodiments, a user's work area have one or more stationary NMD such that the noise map might be generated using a combination of noise data from NMD's that are fixed (e.g., have a stationary, non-moving location in the area) and NMD's that are portable, thereby allowing for changing location as the user wears the NMD and moves about the area. In such instances, the use of noise data from NMD's which are fixed and data from NMD's that are portable allow for enhanced location accuracy in the creation and refreshing of the noise map. This may allow for a system in which a noise map is generated (e.g., for a facility from multiple noise monitoring devices (which might be fixed and/or mobile), and then used to dynamically adjust NMD's with hearing protection capabilities (e.g., with hearing protection elements and/or noise cancellation) so as to improve the safety of and enhance the user's productivity by shielding the worker from dangerous noise levels before they are exposed to them. It should also be understood that embodiments of NMDs that are implemented in systems disclosed herein may or may not have hearing protection features, such that one of ordinary skill in the art would consider a NMD with hearing protection elements to be a type of hearing protection device. The NMDs of the present disclosure may not be required to have hearing protection elements, and thus the user may—in some embodiments—have hearing protection devices that are independent of the NMD's described herein (such that an independent/separate NMD is configured without hearing protection and used alone or in conjunction with a user wearing a separate hearing protection device that does not have noise detection, monitoring, or mapping capabilities). Thus, any reference above to NMD could also include an independent hearing protection device instead of or in addition to, an NMD that has integrated hearing protection elements.

As noted above, in some embodiments the noise map could be used in combination with a worker location tracking system, such that the person/worker not wearing any noise monitoring NMD/hpd could still have their noise exposure data determined and stored by the computer by combining the worker's location throughout the work day compared with the noise levels available through the mapped data (e.g., from the NMD) at the time that such person/worker is located in a given area/zone (with known noise level in such zone(s) due to the noise map) (e.g., correlating such a worker's location with the measured noise data from other NMD). In other words, the noise map could be used in combination with a worker location tracking system, such that a person not wearing a noise monitoring HPD/NMD could still have their noise exposure data stored by the computer (e.g., by combining their detected location throughout the working day compared with the noise levels measured through the mapped data corresponding to such locations for that person). Due to the noise map, we know the noise level in a given area/zone (for example of a facility); so if we know who is working in that area (due to the location tracking system/worker location device) we can calculate their noise exposure (even if the worker moves across multiple zones during the work day). In such embodiments, the location of the worker/user (e.g., without a NMD/hpd) would still be needed, for example via a worker location tracking system and/or worker locator device/unit (which might for example include a locator device worn by the worker/user (e.g., GPS) and/or (fixed/separate/independent) locator device/sensors/system operable/configured to detect user/worker location. Such a worker location tracking system (e.g., which might include a worker locator device) would typically communicate with the computer (e.g., providing worker location data to the computer). The computer could link/correlate worker location data with the noise data of the noise map (and store this calculated noise exposure data in a database) to allow for that worker's estimated (e.g., approximate) noise exposure to be determined. Such an estimated noise exposure could be used to monitor noise exposure without the need for personalized NMD (e.g., worn by the workers) and/or could be used to monitor the noise exposure for certain workers who might not be wearing NMD. For example, this approach may be particularly useful for noise areas/zones that are around the 80-85 dB levels, which are borderline areas that may not normally require the use of hearing protection. In some embodiments, the computer might transmit an alert/warning (e.g., by speaker on the worker locator device or PA system, etc.) to such worker(s) without NMD, for example warning of approaching or exceeding threshold/limit and/or need to move away from the zone (and perhaps directing such worker(s) to a safe zone based on the noise map).

As also noted above, the noise map (e.g., pooled noise data) might also be used to listen for (e.g., detect) equipment malfunction based on noise level changes (e.g., excessive noise, for example above a specific level/threshold) and/or specific detected noise (e.g., specific frequencies), typically outside the norm for the area/zone, and in some instances the location data for (e.g., associated with) the various noise data can be used to interpolate/estimate the location of the malfunction (e.g., the source, perhaps in comparison to prior readings over time). So for example, the pooled noise data from the plurality of noise monitoring devices is actively listening to the machinery of the facility, and detecting abnormalities in the sound of the machinery/equipment may predict machine failures, potential downtimes, and/or need for maintenance. This may allow for rapid deployment of maintenance (personnel), for example possibly in the early stages of malfunction before significant equipment damage occurs or significant risk of injury arises. Similarly, by recording in memory the noise map (pooled noise data) over time, it may be possible to employ noise level/map replay for recreating and/or problem solving (for example in the event of failure and/or alarm event).

Other potential uses of the pooled noise data might include analysis of a dynamic noise map (e.g., pooled noise data over time) to improve job planning system, for example so that the job planning system (which might be software running on the computer) is able to determine/calculate the optimum work time for specified tasks by users based on noise data for a given period of time (e.g., within a work shift), and/or to determine appropriate staffing for specific tasks and/or areas/zones in the facility based on user exposure history and/or individualized hearing threshold or exposure tolerance; and/or preemptively deciding when to add noise cancellation (e.g., at certain frequencies) when threshold for area/zone is approaching, and/or NMD reacting to the environment (e.g., sensed noise as correlated by the noise map) by adjusting hear through or noise cancelling function's within the HPD (for example, in instances other than merely to account for moving noise source as discussed in more detail in sections (a) and (h) above). Furthermore, NMD gathering noise data for correlation into a noise map could also be used in some embodiments for environmental (e.g., external to facility) noise mapping. For example, the noise map could include noise from a facility or from an arrangement (ex: concert) (e.g., external noise projected out of a facility). Under some circumstances, there can be limits to how much noise a facility or arrangement can "let out" (e.g., noise pollution). Under such circumstances, monitoring the noise at the border of the facility or arrangement and/or close to relevant "receivers" (e.g., neighbors) and storing this for documentation might be valuable (for example, to allow for re-engineering to reduce noise pollution). So for example, (fixed) NMD may be located outside (e.g., around the perimeter) of the facility and/or in proximity to relevant receivers (e.g., neighbors), and their noise data could allow the computer to generate a noise map indicative of external noise projected out of the facility (e.g., noise pollution). In some embodiments, the computer might also analyze the noise data to identify specific noise sources (e.g., based on the known frequency range of certain equipment) to help identify particular culprits with respect to noise pollution, which might be candidates for re-engineering to reduce noise. These and other uses for the pooled noise data are contemplated.

Figure 5:
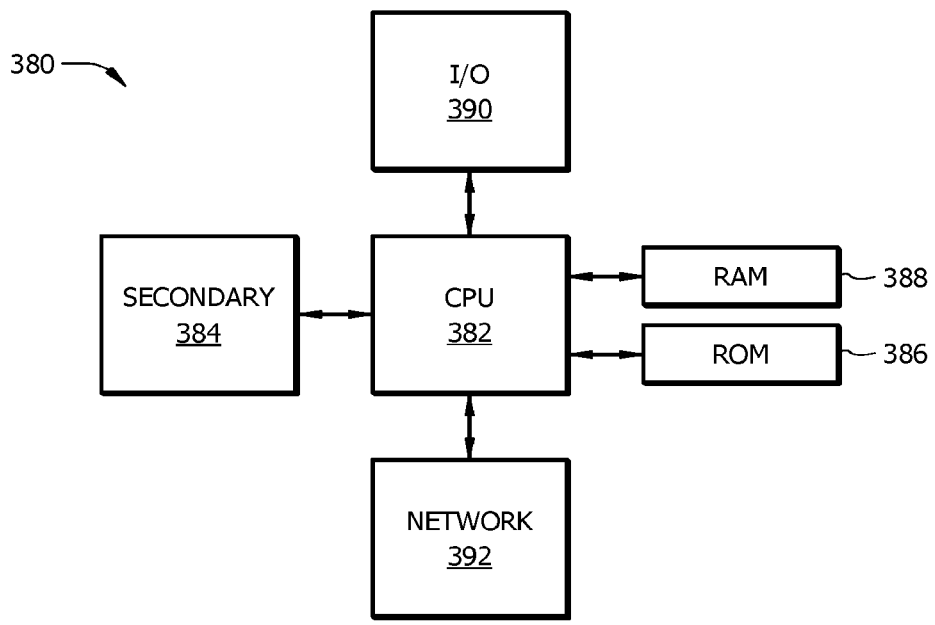
FIG. 5 is a block diagram that illustrates an exemplary computer system suitable for implementing the several embodiments of the disclosure.

FIG. 5 illustrates a computer system 380 suitable for implementing one or more embodiments disclosed herein, such as features of system 100 in FIGS. 1-4, including one or more computer system 160, datastore 156, network node 150, dispenser 140, and operations disclosed iii FIGS. 2, 3A-3D, and 4. The computer system 380 includes a processor 382 (which may be referred to as a central processor unit or CPU) that is in communication with memory devices including secondary storage 384, read only memory (RUM) 386, random access memory (RAM) 388, input/output (I/O) devices 390, and network connectivity devices 392. It is understood that use of the term "memory" in the claims does not include transitory signals. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine, sometimes referred to as a special purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embodied in the carrier wave, or other types of signals currently used or hereafter developed, may be generated according to several methods well-known to one skilled in the art. The baseband signal and/or signal embodied in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprised on one or more non transitory computer readable storage medium having computer usable program code embodied therein to implement the functionality disclosed above. The computer program product may comprise data structures, executable instructions, and other computer usable program code. The computer program product may be embodied in removable computer storage media, non-removable computer storage media, or any combination therein. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

Figure 6:
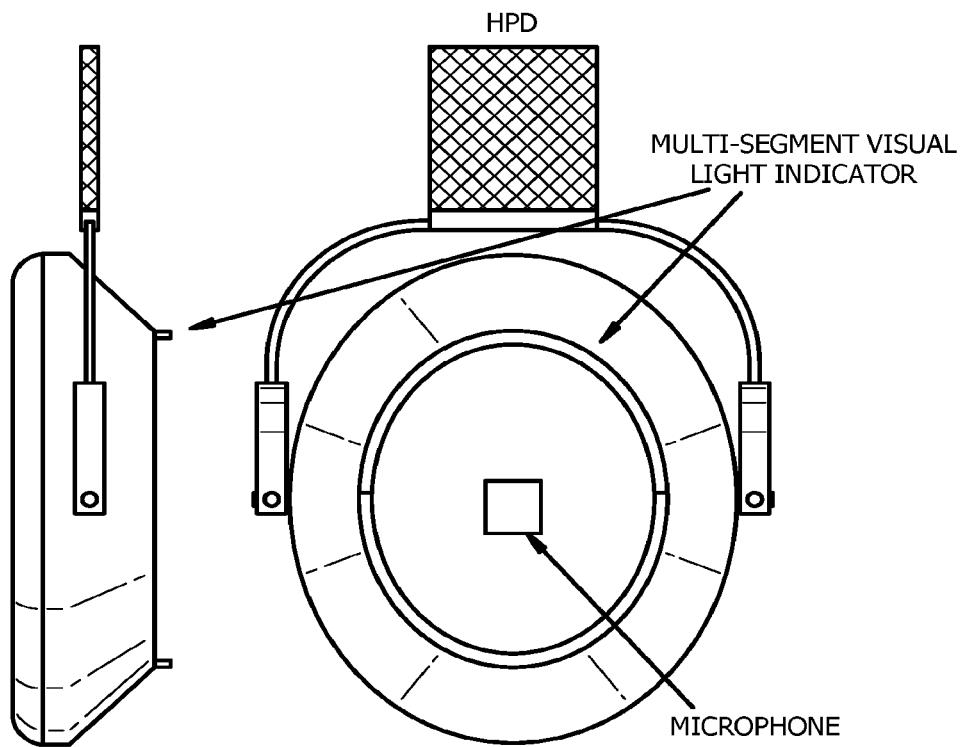
FIG. 6 is a schematic diagram showing an exemplary NMD/hpd with exemplary visual indicator (with both front and side views), showing two exemplary stages of illumination.

In some embodiments, the NMD (such as portable/wearable hpd) may include a visual indicator (e.g., one or more lights) which may relate to and/or be indicative of noise data (for example, with respect to the specific NMD/hpd and/or the zone/area of the facility that the NMD/hpd is located in). FIG. 6 illustrates an exemplary hpd with visual indicator (e.g., multi-segmented visual light indicator, so for example the number of such multi-segmented lights illuminated might vary depending on conditions (e.g., based on the data), such that the illuminated portion might change in size and/or color and/or intensity and/or illumination pattern (e.g., such as flashing/pulsing in one or more rhythms)). In some embodiments, the NMD/hpd could receive data from (e.g., be in communication with) the system/computer (e.g., with noise map data), and the visual indicator might display accordingly (e.g., in response to such data). Visual indicator embodiments could be used for various purposes (e.g., to display various information), including by way of example the following:

1. Using the NMD/hpd to report accumulated exposure for the worker through visual indication to co-workers (e.g., so that the visual indicator is indicative for exposure of the worker wearing the device (for example, showing personal noise exposure of such worker under the hpd)). The NMD/hpd could determine/calculate or receive such a determination/calculation from the system/computer regarding the level of noise exposure of the worker (e.g., despite any hearing protection/attenuation), for example based on a microphone of the NMD/hpd and/or the noise map data from the system/computer (e.g., which calculation might account for the known attenuation of the NMD/hpd). The level of noise dose (e.g., from the calculation) could then be visually indicated on the exterior of the headset using a lighting effect (e.g., using the visual indicator). In other words, if the NMD/hpd has an internal microphone (e.g., underneath the hearing protection element, so as to measure actual noise incident on the worker's ear), then the visual indicator might be illuminated based on the actual measured data from the microphone. If, however, the NMD/hpd has an exterior microphone (configured to measure the external environmental noise level), then the visual indicator might illuminate based on a calculation that uses the measured microphone sound level and the known attenuation of the NMD/hpd (e.g., in order to determine the estimated noise incident on the ear of the worker). On the other hand, such a calculation could use the noise map data (e.g., from the system/computer, representing the external environmental noise level) with the known attenuation of the NMD/hpd in order to determine the amount of illumination of the visual indicator. As shown in FIG. 6, this lighting/illumination of the visual indicator can take the form of a ring of LED or light-guides (e.g., with a plurality of separate lights operable to be separately activated) with light driving electronics mounted within the headset. In some embodiments, the orientation of the lighting (of the visual indicator) can be designed such that the amount of accumulated dose is instantly recognizable (e.g., easily discernible) by a third party some distance from the worker wearing the HDP. In other words, the visual indicator could have lights configured (e.g., angled) to increase visibility for those around the wearer (e.g., so that co-workers can quickly see the wearer's exposure and identify if the wearer has been exposed to a potentially dangerous level of noise exposure (e.g., if there is a warning/alert situation)). For example, the visual indicator might have its lights oriented to ensure effective visibility from essentially any angle around the worker wearer. Such an approach may allow a surrounding third-party (e.g., co-worker) to determine if the worker wearer is close to or has exceed the maximum limit for noise for that particular period of time, and this may allow the co-workers to provide an extra check on hearing safety (for example, if the wearer does not notice or intentionally disregards the danger). In some embodiments, the visual indicator can have multiple configurations (e.g., depending on the specifics of illumination of the visual indicator). For example, the configuration of the light indicator may have 2 or more (e.g., multiple) color changing segments, and each segment could change color (ex. by deactivating one color LED and activating another color LED in that segment) or brightness or illuminate representing a progressing increase in noise exposure for the worker. In some embodiments, each side of the headset or other NMD/hpd could be configured to represent the noise exposure for the corresponding ear, while in other embodiments both left and right sides could display the same exposure level (e.g., average exposure). The color and brightness of each visual segment can be configured.

2. Using the visual indicator of the NMD/hpd to report/indicate (external) noise level of the environment in which the NMD/hpd user is working through visual indication to co-workers (such that the visual indicator is indicative of the environmental noise level for the section/area). The NMD/hpd could determine/calculate or receive such a determination/calculation from the system/computer regarding the level of noise of the zone/area in which the NMD/hpd is located (e.g., the environmental noise level)), for example based on a microphone of the NMD/hpd and/or the noise map data from the system/computer. The level of environmental noise (e.g., from the calculation) could then be visually indicated on the exterior of the headset using a lighting effect (e.g., using the visual indicator). In other words, if the NMD/hpd has an internal microphone (e.g., underneath the hearing protection element, so as to measure noise incident on the worker's ear), then the visual indicator might be illuminated based on a calculation using the measured noise level from the microphone and the known attenuation of the NMD/hpd (e.g., accounting for the attenuation to calculate how loud the external environment outside the hpd would be). If, however, the NMD/hpd has an exterior microphone (configured to measure the external environmental noise level), then the visual indicator might illuminate based on the actual measured microphone sound level. On the other hand, such a calculation (regarding illumination of the visual indicator) could use the noise map data (e.g., from the system/computer, representing the external environmental noise level) to determine the amount of illumination of the visual indicator. As shown in FIG. 6, this lighting/illumination of the visual indicator can take the form of a ring of LED or light-guides (e.g., with a plurality of separate lights operable to be separately activated) with light driving electronics mounted within the headset. When working in external noise environments, the noise level visualization (e.g., provided by the visual indicator) can provide an immediate indication of the presence of dangerous noise levels and prompt any approaching or surrounding worker to don their HPD (in other words, the hope is that such a visual indicator of external noise environment which is visible to other co-workers will help such co-workers to realize if and when they should don their own hearing protection devices). This could be particularly helpful if not all workers in an area/zone have the more advanced type of NMD/hpd (e.g., with microphone and/or warning capabilities), since those other co-workers might be able to take their cues from their fellow workers who do have more advanced NMD/hpd (e.g., based on such visual indicator cues). And as discussed above, if working within an area that benefits from the noise map (e.g., with NMD/hpd as part of a system as described herein), the system can communicate the level of noise of the zone/area to the NMD/hpd (by the means described previously), so that the light visualization (e.g., of the visual indicator) on the headset represents the level of noise of the zone/area in which the headset is located (e.g., using the location information from the NMD in conjunction with the noise map data, the computer may communicate with the NMD regarding the illumination of the visual indicator, so that the visual indicator illuminates to show the environmental noise level of the zone/area in which the NMD is currently located). In some embodiments, the orientation of the lighting (of the visual indicator) can be designed such that the environmental noise level is instantly recognizable (e.g., easily discernible) by a third party some distance from the worker wearing the hdp. In other words, the visual indicator could have lights configured (e.g., angled) to increase visibility for those around the wearer (e.g., so that co-workers can quickly see and identify the noise level of the current environment (e.g., if it is sufficiently high that hpd should be donned)). For example, the visual indicator might have its lights oriented to ensure effective visibility from essentially any angle around the worker wearer. Such an approach may allow a surrounding third-party (e.g., co-worker) to determine the environmental noise level by observing the NMD/hpd (of another), so for example they might know when to don their hpd (even if their own hpd is relatively simple (e.g., no microphone) and/or is not part of the system). The specific environmental noise level data shown by the visual indicator could be instantaneous, dynamic, and/or continuous (as discussed above). For example, the device could be configured so that the environmental noise level might be reported over a period of time such as 1, 2, 3, 5, 15, or more minutes, for example representing the time-averaged value over such time period (as discussed above). In some embodiments, the visual indicator can have multiple configurations (e.g., depending on the specifics of illumination of the visual indicator). For example, the configuration of the light indicator may have 2 or more (e.g., multiple) color changing segments, and each segment could change color (e.g., by deactivating one color LED and activating another color LED in that segment) or brightness/intensity or illuminate representing a progressing increase in in noise levels within the immediate environment of the NMD/hpd user. In some embodiments, each side of the headset or other NMD/hpd could be configured to represent the noise level for the corresponding side, while in other embodiments both left and right sides could display the same exposure level (e.g., average exposure or the highest exposure level). The color and brightness of each visual segment can be configured.

3. Using the visual indicator to report/indicate whether fit or seal of hpd is adequate In some embodiments, the NMD/hpd could automatically sample the external noise (for example, either using an external microphone and/or the noise map from the system/computer) and compare it to the internal noise level (e.g., detected by an internal microphone), in order to determine if the NMD/hpd hearing protection (e.g., attenuation) element(s) are functioning properly (e.g., whether there is a good fit/seal, or whether the hpd should be repositioned to achieve a better fit/seal). For example, if the delta (e.g., difference) between the two noise levels (internal and external) is below a set value, the light guide may alert (e.g., the visual indicator could illuminate to indicate poor fit) In the situation with a noise map (as discussed herein), the NMD location data can be used with the noise map to determine the external noise environment (for example, if the NMD/hpd only has an internal microphone). This external noise data from the system/computer can then be compared to the measured internal noise level (under the hpd, for example measured via an internal microphone). This approach may give an indication of a person at risk of getting an over exposure before the overexposure is a fact. Similar to the discussion above, the visual indicator can be oriented so as to be clearly visible to co-workers (so that they may notice if there is a poor fit and inform the wearer, to serve as a second check).

4. Using the hpd visual indication to increase workers visibility in low-light conditions or to represent an alarm situation for the worker. As a potential side benefit to such NMD/hpd with visual indicator, the light indicator on the headset could be configured to display a pre-configured pattern with a specific light color and/or intensity such that the light effect can be enabled when working in dark or unlit conditions. For example, the NMD/hpd might be configured with a light detector, and when it detects a pre-set low level of light (or less), it activates the visual indicator in such a way as to increase worker visibility. Alternatively, the system might have such light detectors (for example, at least one per zone), and might communicate with the specific NMD/hpd in areas of low light (based on the NMD/hpd location data) to activate their visual indicator in such a way as to increase worker visibility. Worker visibility could relate to the ability of the worker to see (e.g., illuminating the area around the worker to help them see better) and/or making the worker more visible to others (e.g., so co-workers can clearly see the location of the worker wearer, to avoid collisions for example). In some embodiments, flashing, strobe or repeating (lighting) effect for the visual indicator may create a higher visibility for the worker from a distance and/or can bring attention to the worker if in distress (e.g., such higher visibility light effects might only be activated in response to an indication (from the NMD/hpd itself (such as a sensor mounted thereon) and/or the system/computer in communication with the NMD/hpd (e.g., based on a sensor, etc.)) that there is some sort of worker distress (e.g., by the worker wearing the NMD/hpd) which needs attention). As described above, the visual indicator may in some instances be oriented to increase visibility for third parties (e.g., co-workers).

Having described above various system and method embodiments, various additional embodiments may include, but are not limited to the following:

In a first embodiment, a system may comprise a plurality of noise monitoring devices (NMD), each comprising: a microphone and processor for noise monitoring/detection (of external and/or internal noise in the surrounding environment in proximity to the NMD); a locator device (such as GPS, Active RFID, WiFi, Bluetooth, Infrared, and/or Ultrasonic Ranging) operable/configured to determine the location of the NMD (for example, within a facility); and a (wireless) communication device (e.g., wireless transmitter/receiver or transceiver, or in some embodiments, a wired communication device (for example for fixed NMD)) (e.g., configured to communicate with or between other NMD (e.g., with the interconnected processors of the NMD performing computing tasks, and/or cloud computing and/or some other form of distributed computing performing computing tasks) and/or a separate computer (for performing computing tasks)—and wherein the computing tasks may include pooling noise data from the plurality of NMD, e.g., to create a noise map).

A second embodiment can include the system of the first embodiment, wherein one or more of the NMD comprises a hearing protection element (e.g., earmuff, earplug, or other element for sealing the ear canal or otherwise protecting the user from external noise) (such that the NMD would be a hearing protection device (hpd) configured to detect noise exposure).

A third embodiment can include the system of the first or second embodiment, further comprising a remotely located computer/processor (such as a central station computer, comprising a wireless communication device (e.g., wireless received/transmitter or transceiver) configured to: communicate with the plurality of NMD; and use (e.g., pool) the noise monitoring data communicated from the plurality of NMD to generate a noise map; wherein the plurality of NMD are communicatively connected with the computer.

A fourth embodiment can include the system of any of the first through third embodiments, wherein the noise map may be or comprise dynamic and/or accumulated over time (e.g., cumulative) and/or instantaneous.

A fifth embodiment can include the system of any of the first through fourth embodiments, wherein the remotely located computer further comprises a display (e.g., a screen) configured/operable to display the noise map (of the facility).

A sixth embodiment can include the system of any of the first through fifth embodiments, wherein the remotely located computer is configured to extrapolate/interpolate for areas of the noise map between the actual measured noise monitoring data points received by the computer from the plurality of NMD.

A seventh embodiment can include the system of any of the first through sixth embodiments, wherein the computer is configured to determine from noise monitoring data (from the communicatively connected NMD) a moving noise source.

An eighth embodiment can include the system of the seventh embodiment, wherein the computer is configured to compare the detected noise to a database of known sounds to determine what is the cause of the moving noise source (e.g., what type of vehicle or other machinery is the likely cause of the moving noise).

A ninth embodiment can include the system of the seventh or eighth embodiment, wherein the computer is configured to extrapolate/project the trajectory/course of the moving noise source (which could be displayed on the screen of the computer).

A tenth embodiment can include the system of the ninth embodiment, wherein the computer is further configured to determine if any NMD are located along the trajectory of the moving noise source and to send a warning to any such NMD along the trajectory (so that the user can be aware of a possible physical danger that they might not hear due to wearing of hpd, for example).

An eleventh embodiment can include the system of the tenth embodiment, wherein the computer is further configured to consider movement of NMD to see if it likely intercepts the trajectory of the moving noise source and need to send warning.

A twelfth embodiment can include the system of the tenth or eleventh embodiment, wherein the warning might comprise one or more of the following: a sound beacon/tone/beeping that varies in volume based on proximity to moving noise source (e.g., volume increases as moving noise source approaches NMD/hpd); adjust hear-through (so user more likely to hear moving noise source and be able to avoid); vibration that varies in intensity based on proximity to moving noise source; change to tactility, etc.

A thirteenth embodiment can include the system of any of the first through twelfth embodiments, wherein the computer is further configured to detect an (audible) alarm (e.g., from a speaker of a PA system, for example via noise data received from one or more NMD) and transmit/share such alarm info, with other NMD in zone of alarm and/or related zone(s) (e.g., in proximity or abutting the alarm zone).

A fourteenth embodiment can include the system of the thirteenth embodiment, wherein the computer is further configured to detect if a NMD is (in an adjacent zone and) moving towards the alarm zone (based on trajectory of NMD movement based on location data over time) and transmits a warning (e.g., pre-alarm) to such NMD.

A fifteenth embodiment can include the system of any of the first through fourteenth embodiments, wherein the NMD is associated with a user; and wherein the computer further comprises a database of individual user hearing test data (e.g., threshold/exposure tolerance for specific individual users) and the computer is further configured to correlate user location with noise level and compare to database to determine if a warning should be sent to a user (for example, if the specific user is sensitive and should not be exposed to such loud noise, even if the noise level is below the standard threshold).

A sixteenth embodiment can include the system of the fifteenth embodiment, wherein the computer is configured to transmit a warning to the user recommending movement to another zone and/or away from a specific zone based on the noise map (e.g., in relation to the user's threshold/exposure tolerance information and/or the detected noise from other zones (e.g., noise map data)).

A seventeenth embodiment can include the system of the fifteenth or sixteenth embodiments, wherein the computer is further configured to detect if a NMD is (in an adjacent zone and) moving towards the zone having noise in excess of the user's threshold/exposure tolerance (based on trajectory of NMD movement based on location data over time) and transmits a warning (e.g., recommendation) to such NMD (e.g., regarding the amount of time the user might spend in that zone and/or an alternative zone better suited to the user).

An eighteenth embodiment can include the system of the first through seventeenth embodiments, wherein, for a new worker coming in (for example, into a facility or zone), the computer is configured to determine the zone (of the noise map/facility) that the user will be entering and suggest/ recommend or provide (e.g., automatically dispense) appropriate hpd/NMD based on noise map.

A nineteenth embodiment can include the system of any of the first through eighteenth embodiments, wherein the computer is further configured to compare information on the location and type of hpd/NMD to the noise map, determine if hpd/NMD is insufficient/inadequate, and transmit a warning to the hpd/NMD if it is found inadequate.

A twentieth embodiment can include the system of the nineteenth embodiment, wherein the computer is further configured to generate an estimate of time to spend in the zone (based on location, type of hpd/NMD, and noise map) and transmit to the hpd/NMD.

A twenty-first embodiment can include the system of any of the first through twentieth embodiments, wherein the computer is configured to use noise monitoring data (e.g., from the noise map) regarding a moving noise source to alter the set-up/configuration of hpd/NMD along the trajectory of the moving noise source (e.g., alter/tune active noise cancellation for any hpd/NMD along the course of trajectory of the moving noise source based on information from other hpd/NMD regarding that moving noise source (e.g., in order to earlier make adjustments)).

A twenty-second embodiment can include the system of any of the first through twenty-first embodiments, wherein the computer is further configured to detect if a hpd/NMD is moving towards the trajectory of the moving noise source (based on trajectory of hpd/NMD movement based on location data over time) and alters the set-up/configuration of such hpd/NMD.

A twenty-third embodiment can include the system of any of the first through twenty-second embodiments, further comprising one or more fixed noise monitoring/detecting devices (e.g., having a microphone, processor, and wireless communication device configured/operable to communicate with the computer and/or plurality of NMD (for example, at least one such fixed NMD per zone).

A twenty-fourth embodiment can include the system of any of the first through twenty-third embodiments, wherein the computing tasks (e.g., performed by the computer) comprises population wide analysis of areas/zones within a facility that may need to be engineered to reduce noise emissions, based on the noise map.

A twenty-fifth embodiment, can include the system of any of the first through twenty-fourth embodiments, wherein the computing tasks (e.g., performed by the computer) comprises using noise detection information (e.g., the noise map) for fault detection (for example to detect part or equipment failure based on noise level outside the expectation (e.g., range) for a zone/area (for example based on pre-knowledge of what an area/zone should sound like and/or based on specific frequency detection indicative of such a failure) and/or help locate such failures by correlating data from several noise monitoring devices to determine location, which can then be used to notify maintenance).

A twenty-sixth embodiment can include the system of any of the first through twenty-fifth embodiments, further comprising a worker location tracking system (such as one or more worker locator devices) operable to determine the location of any workers within a zone/area/facility not wearing NMD/hpd (and in some embodiments, any such worker locator devices might be separate from the NMD/hpd), wherein the computer receives worker location data and correlates that worker location data with the noise data (e.g., from a noise map developed from the NMD)) to determine such worker's estimated noise exposure.

A twenty-seventh embodiment can include the system of the twenty-sixth embodiment, wherein at least some (e.g., at least one) workers do not have/wear NMD (e.g., they only have a separate worker location device).

A twenty-eighth embodiment can include the system of the twenty-sixth or twenty-seventh embodiments, wherein the computer is configured to send an alert (e.g., to the worker locator device or via PA system, etc.) to any worker not wearing NMD when the worker's estimated noise exposure approaches or reaches threshold/limit.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises", "includes", and "having" should be understood to provide support for narrower terms such as "consisting of", "consisting essentially of", and "comprised substantially of". Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

Having described the various systems and methods herein, various embodiments of the systems and methods can include, but are not limited to the claims provided herein.

The invention claimed is:

1. A system comprises:
a plurality of noise monitoring devices (NMDs); and
a remotely located computer system communicatively coupled to the plurality of NMDs,
wherein a respective NMD of the plurality of NMDs comprises a microphone electrically coupled to a circuit having a processor and a non-transitory memory, the circuit being configured to:
detect incoming noise signals via the microphone,
determine, by a locator unit of the respective NMD, a geolocation of the respective NMD, and
transform the noise signals and the geolocation of the respective NMD into noise data associated with the respective NMD, and
wherein the remotely located computer system is configured to:
receive the noise data associated with the respective NMD and noise data associated with one or more other NMDs of the plurality of NMDs, the noise data associated with the one or more other NMDs comprising corresponding geolocation information of the one or more other NMDs,
adjust the geolocation of the respective NMD based on information of a corresponding location error of the one or more other NMDs,
generate, for the respective NMD, a noise map indicating a noise exposure level at the corresponding geolocation of the respective NMD, the noise map comprising a plurality of zones demarcated based on the noise data associated with the respective NMD and the noise data associated with the one or more other NMDs of the plurality of NMDs, and
in an instance in which the noise exposure level at the corresponding geolocation of the respective NMD approaches or exceeds a predetermined threshold, recommend a user to relocate from a current zone to another zone of the plurality of zones based on the noise map.

2. The system of claim 1, the circuit being configured to:
transform the noise signals into the noise data associated with the respective NMD by appending values obtained from the noise signals with geolocation coordinates received from the locator unit.

3. The system of claim 2, the circuit being configured to:
include an identifier of the respective NMD into the noise data; and
cause periodic transmission of the noise data in response to at least one of a passage of a predefined time period, an external request received via a network, or a combination of the predefined time period and the external request.

4. The system of claim 3, further comprising:
a transceiver electrically coupled to the processor of the circuit, the transceiver being configured to periodically transmit the noise data via the network.

5. The system of claim 1, wherein the remotely located computer system is communicatively coupled via a network to the plurality of NMDs, the remotely located computer system comprising a transceiver coupled to a processor and a non-transitory memory, the non-transitory memory comprising an application that, upon execution, configures the remotely located computer system to:
pool the noise data associated with the respective NMD and the noise data associated with the one or more other NMDs of the plurality of NMDs; and
based on the pooled noise data, generate the noise map.

6. The system of claim 5, wherein the respective NMD further comprises a display configured to present the noise map in response to reception of the noise map from the remotely located computer system, wherein the noise map is updated on the display by the remotely located computer system, wherein either a color or a brightness of the plurality of zones demarcated in the noise map corresponds to an intensity of noise.

7. The system of claim 5, wherein the remotely located computer system is further configured to:
determine whether at least one NMD of the plurality of NMDs is located along a trajectory path corresponding to a moving noise source; and
in an instance in which the trajectory path of the moving noise source will result in a noise exposure level at a current location of the at least one NMD that approaches or exceeds a predetermined threshold for respective users of the at least one NMD, push at least an audio alarm to the at least one NMD located along the trajectory path, wherein the audio alarm transmits an audible warning indicating presence of a noise source within a defined time period.

8. The system of claim 1, wherein the remotely located computer system is coupled to a datastore that stores hearing test data comprising noise exposure thresholds for users, and the remotely located computer system is further configured to correlate the geolocation information with the noise signals from the noise data to determine the noise exposure level for the user of the respective NMD, and compare the noise exposure level to a noise exposure threshold from the respective NMD user's hearing test data in the datastore to determine if a warning should be sent to the respective NMD in response to the noise exposure level approaching or exceeding the noise exposure threshold while at a current geolocation of the respective NMD.

9. The system of claim 5, wherein the remotely located computer system is further configured to:
identify a direction and a speed of movement of a noise source by comparing at least noise data and geolocation data associated with one or more NMDs of the plurality of NMDs which indicate an increase during a first period of time in an intensity of the noise exposure level to noise data and geolocation data associated with one or more other NMDs of the plurality of NMDs which indicate a decrease during the first period of time in the intensity of the noise exposure level relative to the respective geolocations of the one or more NMDs and the one or more other NMDs;
predict a trajectory of the noise source by extrapolating the direction and speed of movement of the noise source during a second period of time following the first period of time;
overlay the trajectory on the noise map to provide a trajectory path of the moving noise source; and
update the noise map to include a visual representation of the trajectory path of the noise source.

10. A method to monitor and map noise data from a plurality of noise monitoring devices (NMDs), the method comprising:
detecting incoming noise signals via a microphone of a respective NMD of the plurality of NMD s;
determining, by a locator unit of the respective NMD, a geolocation of the respective NMD;
transforming the noise signals and the geolocation of the respective NMD to noise data associated with the respective NMD;
receiving, at a remotely located computer system communicatively coupled to the plurality of NMDs, the noise data associated with the respective NMD and noise data associated with one or more other NMDs of the plurality of NMDs, the noise data associated with the one or more other NMDs comprising corresponding geolocation information of the one or more other NMDs;
adjusting the geolocation of the respective NMD based on information of a corresponding location error of the one or more other NMDs,
generating a noise map indicating a noise exposure level at the corresponding geolocation of the respective NMD, the noise map comprising a plurality of zones demarcated based on the noise data associated with the respective NMD and the noise data associated with the one or more other NMDs of the plurality of NMDs; and in an instance in which the noise exposure level at the corresponding geolocation of the respective NMD approaches or exceeds a predetermined threshold, recommending a user relocate from a current zone to another zone of the plurality of zones based on the noise map.

11. The method of claim 10, further comprising:
transforming the noise signals into the noise data associated with the respective NMD by appending values obtained from the noise signals with geolocation coordinates received from the locator unit of the respective NMD.

12. The method of claim 10, further comprising:
including an identifier of the respective NMD into the noise data; and
instructing a transceiver to at least periodically transmit the noise data in response to at least one of a passage of a predefined time period, an external request received via a network, or a combination of the predefined time period and the external request.

13. The method of claim 10, further comprising:
pooling, using the remotely located computer system, the noise data associated with the respective NMD and the noise data associated with the one or more other NMDs of the plurality of NMDs, and
based on the pooled noise data, generating the noise map.

14. The method of claim 13, further comprising:
presenting, via a display of the respective NMD, the noise map, wherein the noise map is updated on the display of the respective NMD by the remotely located computer system, wherein either a color or a brightness of the plurality of zones demarcated in the noise map corresponds to an intensity of noise.

15. The method of claim 13, further comprising:
determining, via the remotely located computer system, whether at least one NMD of the plurality of NMDs is located along a trajectory path corresponding to a moving noise source; and
in an instance in which the trajectory path of the moving noise source will result in a noise exposure level for the at least one NMD that approaches or exceeds the predetermined threshold for a user of the at least one NMD, pushing at least an audio alarm to the at least one NMD located along the trajectory path, wherein the audio alarm transmits an audible warning indicating presence of a noise source within a defined time period.

16. The method of claim 15, wherein the audio alarm comprises one or more of the following:
an audible sound that, when transmitted through speakers coupled to the at least one NMD, varies in volume based on proximity of the noise source such that the volume increases as the noise source approaches the at least one NMD;
an instruction to the circuit of the at least one NMD that adjusts a hear-through configuration setting of noise cancellation such that the at least one NMD decreases noise cancellation and allows sound above the predefined threshold to pass to the ear canal of the user, thereby increasing the likelihood that the user hears the audio alarm;
an instruction, to a vibration device electrically coupled to the at least one NMD, to induce a vibration that varies in intensity based on proximity of the at least one NMD to the noise source moving along the trajectory path; and
an instruction to change tactility of an interface of the at least one NMD.

17. The method of claim 10, wherein the remotely located computer system comprises or is communicatively coupled to a datastore that stores hearing test data comprising sound exposure thresholds associated with users of the plurality of NMDs, the method further comprising:
- correlating, using the remotely located computer system, the geolocation with the noise signals from the noise data received from the respective NMD to determine the noise exposure level for the user of the respective NMD; and
- comparing the noise exposure level to a noise exposure threshold in the datastore associated with the user of the respective NMD to determine if a warning should be sent to the respective NMD in response to the noise exposure level approaching or exceeding the noise exposure threshold associated with the user of the respective NMD while at the geolocation of the respective NMD.

18. The method of claim 13, further comprising:
- identifying a direction and a speed of movement of a noise source by comparing at least noise data and geolocation data associated with one or more NMDs of the plurality of NMDs that indicate an increase during a first period of time in an intensity of the noise exposure level to noise data and geolocation data associated with one or more other NMDs of the plurality of NMDs that indicate a decrease during the first period of time in the intensity of the noise exposure level relative to the respective geolocations of the one or more NMDs and the one or more other NMDs;
- predicting a trajectory of the noise source by extrapolating the direction and speed of movement of the noise source during a second period of time following the first period of time;
- overlaying the trajectory on the noise map to provide a trajectory path of the moving noise source; and
- updating the noise map to include a visual representation of the trajectory path of the noise source.

19. The method of claim 10, further comprising:
- detecting, if the respective NMD is in a zone adjacent to a noise source, based at least upon the geolocation determined for the respective NMD over time, a trajectory of movement of the respective NMD, and whether the respective NMD is moving towards the zone in which the noise source is currently located; and
- in response to detecting that the respective NMD is moving towards the zone in which the noise source is located, transmitting a message to the respective NMD, wherein the message is configured for one or more of: alerting the user of the respective NMD to the noise source, causing adjustment of noise cancellation by the respective NMD, or providing or displaying directions to a nearest hearing protection dispenser.

20. The method of claim 10, further comprising:
- detecting if the respective NMD is in a zone adjacent to a zone in which the noise source is currently located or if the respective NMD is moving towards another zone having a noise level in excess of the predetermined threshold for the user of the respective NMD, wherein detection is based on a trajectory of movement of the respective NMD, the trajectory of movement being calculated using at least the geolocation associated with the respective NMD; and
- in an instance in which the respective NMD is in a zone adjacent to the one in which the noise source is currently located or the respective NMD is moving towards another zone having a noise level in excess of the predetermined threshold for the user of the respective NMD, transmitting a warning to the respective NMD, wherein the warning indicates an amount of time the user has remaining to spend in the adjacent zone or the another zone as well as a recommendation for the user of the respective NMD to relocate to a further zone that has a noise exposure level not in excess of the predetermined threshold for the user of the respective NMD, the recommendation being determined using at least the noise map.

* * * * *